(12) United States Patent  
Ishizuka et al.

(10) Patent No.: US 11,229,895 B2  
(45) Date of Patent: *Jan. 25, 2022

(54) CHEMICAL REACTION METHOD USING CHEMICAL REACTION APPARATUS

(71) Applicant: Microwave Chemical Co., Ltd., Osaka (JP)

(72) Inventors: Akinori Ishizuka, Osaka (JP); Iwao Yoshino, Osaka (JP); Kunitaka Momota, Osaka (JP); Yasunori Tsukahara, Osaka (JP)

(73) Assignee: MICROWAVE CHEMICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/655,533

(22) Filed: Oct. 17, 2019

(65) Prior Publication Data

US 2020/0047148 A1 Feb. 13, 2020

Related U.S. Application Data

(63) Continuation-in-part of application No. 15/398,877, filed on Jan. 5, 2017, now Pat. No. 10,464,040, which (Continued)

(30) Foreign Application Priority Data

Nov. 11, 2011 (JP) ................................. 2011-247954

(51) Int. Cl.
*B01J 19/24* (2006.01)
*C07C 67/08* (2006.01)
(Continued)

(52) U.S. Cl.
CPC ................ *B01J 19/24* (2013.01); *B01J 8/20* (2013.01); *B01J 8/36* (2013.01); *B01J 19/126* (2013.01);
(Continued)

(58) Field of Classification Search
CPC ........ B01J 19/24; B01J 8/20; B01J 8/36; B01J 19/126; B01J 19/18; B01J 19/1862;
(Continued)

(56) References Cited

U.S. PATENT DOCUMENTS 3,170,769 A 2/1965 Stiles et al.
3,463,627 A 8/1969 Le Blanc
(Continued)

FOREIGN PATENT DOCUMENTS

CN 1729049 A 2/2006
CN 1946477 A 4/2007
(Continued)

OTHER PUBLICATIONS

Chinese Office Action dated Feb. 17, 2015 which issued during prosecution of CN Application No. 201280062750.0.
(Continued)

*Primary Examiner* — Xiuyu Tai
(74) *Attorney, Agent, or Firm* — Troutman Pepper Hamilton Sanders LLP

(57) ABSTRACT

A chemical reaction method includes preparing a chemical reaction apparatus including a horizontal flow reactor partitioned into multiple chambers by multiple partition plates. A liquid content horizontally flows with an unfilled space provided thereabove. a microwave generator and a waveguide that transmits microwaves to the unfilled space are also included. The reactor is inclined such that, in each of the chambers, a weir height on an inlet side is higher than a weir height on an outlet side by at least an overflow depth at the partition plate on the outlet side. The content is flowed over each of the multiple partition plates inside the reactor. The content flowing inside the reactor is irradiated with microwaves. The inclination angle of the reactor is changed in
(Continued)

each of the chambers so that a weir height on an inlet side is higher than a weir height on an outlet side.

5 Claims, 25 Drawing Sheets

Related U.S. Application Data is a continuation of application No. 14/357,145, filed as application No. PCT/JP2012/079152 on Nov. 9, 2012, now Pat. No. 9,573,112.

(51) Int. Cl.
| | |
|---|---|
| H05B 6/78 | (2006.01) |
| H05B 6/80 | (2006.01) |
| B01J 8/20 | (2006.01) |
| B01J 8/36 | (2006.01) |
| B01J 19/18 | (2006.01) |
| B01J 19/12 | (2006.01) |
| C07C 67/03 | (2006.01) |

(52) U.S. Cl.
CPC ............ B01J 19/18 (2013.01); B01J 19/1862 (2013.01); C07C 67/03 (2013.01); C07C 67/08 (2013.01); H05B 6/78 (2013.01); H05B 6/806 (2013.01); *B01J 2208/00442* (2013.01); *B01J 2208/00867* (2013.01); *B01J 2219/00141* (2013.01); *B01J 2219/1215* (2013.01); *B01J 2219/1218* (2013.01); *B01J 2219/1245* (2013.01); *B01J 2219/1266* (2013.01); *B01J 2219/1269* (2013.01); *B01J 2219/1293* (2013.01); *B01J 2219/1296* (2013.01); *B01J 2219/182* (2013.01); *B01J 2219/187* (2013.01)

(58) Field of Classification Search
CPC .... B01J 2208/00442; B01J 2208/00867; B01J 2219/00141; B01J 2219/1215; B01J 2219/1218; B01J 2219/1245; B01J 2219/1266; B01J 2219/1269; B01J 2219/1293; B01J 2219/1296; B01J 2219/182; B01J 2219/187; B01J 3/04; B01J 8/1836; B01J 19/0013; B01J 19/245; B01J 2208/00132; B01J 2208/00141; B01J 2208/0084; B01J 2219/00081; B01J 2219/0083; B01J 2219/00108; B01J 2219/00768; B01J 2219/185; B01J 2219/1943; C07C 67/03; C07C 67/08; C07C 51/265; C07C 63/26; H05B 6/78; H05B 6/806; H05B 6/784; C03B 5/023; C03B 5/182; F27B 3/20; F27B 3/18; F27B 3/045; F27B 3/19; F27D 99/0006; F27D 19/00; F27D 2099/0028; B01D 19/0042; B01D 19/0036; E21B 43/36; E21B 21/062; B28C 7/0418; B28C 7/0422; B01F 13/1013; B01F 15/00207; B01F 15/00233; B01F 13/1016; B01F 7/16; F28D 8/1836; F28D 7/0066; F28D 7/0091; G05D 21/02
See application file for complete search history.

(56) References Cited

U.S. PATENT DOCUMENTS

| | | |
|---|---|---|
| 4,269,805 A | 5/1981 | Schoengen et al. |
| 4,279,722 A | 7/1981 | Kirkbride |
| 4,718,358 A | 1/1988 | Nomi et al. |
| 4,844,838 A | 7/1989 | Ohtsuka et al. |
| 5,393,320 A | 2/1995 | Gomez |
| 5,458,897 A | 10/1995 | Pare |
| 5,822,879 A | 10/1998 | Vincent et al. |
| 6,484,539 B1 | 11/2002 | Nordine et al. |
| 6,723,999 B2 | 4/2004 | Holl |
| 7,087,220 B2 | 8/2006 | Li |
| 7,348,182 B2 | 3/2008 | Martin et al. |
| 8,328,997 B2 | 12/2012 | Charlier De Chily et al. |
| 10,464,040 B2* | 11/2019 | Ishizuka ................. C07C 67/03 |
| 2002/0023922 A1 | 2/2002 | Lee et al. |
| 2003/0066792 A1 | 4/2003 | Xia et al. |
| 2004/0056026 A1 | 3/2004 | Jakes et al. |
| 2006/0228088 A1 | 10/2006 | Charlier De Chily et al. |
| 2006/0237300 A1 | 10/2006 | Stroder et al. |
| 2007/0295717 A1 | 12/2007 | Horikawa et al. |
| 2010/0025227 A1 | 2/2010 | Charlier De Chily et al. |
| 2010/0172202 A1 | 7/2010 | Borgstadt |
| 2010/0212492 A1* | 8/2010 | Miotto ............... B01D 19/0042 95/22 |
| 2011/0263843 A1 | 10/2011 | Watanabe et al. |
| 2013/0102047 A1 | 4/2013 | Ishizuka et al. |
| 2013/0102804 A1 | 4/2013 | Charlier De Chily et al. |
| 2014/0121395 A1 | 5/2014 | Ishizuka et al. |
| 2014/0363348 A1 | 12/2014 | Ishizuka et al. |
| 2015/0004069 A1 | 1/2015 | Ishizuka et al. |

FOREIGN PATENT DOCUMENTS

| | | |
|---|---|---|
| CN | 101954266 A | 1/2011 |
| EP | 0626871 A1 | 12/1994 |
| EP | 2385146 A1 | 11/2011 |
| EP | 2727647 A1 | 5/2014 |
| EP | 2845645 A1 | 3/2015 |
| JP | S51/041679 A | 4/1976 |
| JP | S52/35350 A | 3/1977 |
| JP | S58128140 A | 7/1983 |
| JP | S59004431 A | 1/1984 |
| JP | S63/198899 A | 8/1988 |
| JP | S63/285121 A | 11/1988 |
| JP | S63264134 A | 11/1988 |
| JP | H0266497 A | 3/1990 |
| JP | H03/109296 U | 11/1991 |
| JP | H06041545 A | 2/1994 |
| JP | H07/258117 A | 10/1995 |
| JP | H07309433 A | 11/1995 |
| JP | H08501016 A | 2/1996 |
| JP | H08242783 A | 9/1996 |
| JP | H09285282 A | 11/1997 |
| JP | H1050470 A | 2/1998 |
| JP | 2001009009 A | 1/2001 |
| JP | 2002061847 A | 2/2002 |
| JP | 2002/079078 A | 3/2002 |
| JP | 2004/201967 A | 7/2004 |
| JP | 2004/216200 A | 8/2004 |
| JP | 2006511775 A | 4/2006 |
| JP | 2006512554 A | 4/2006 |
| JP | 2006/516008 A | 6/2006 |
| JP | 2006/257304 A | 9/2006 |
| JP | 2007/000774 A | 1/2007 |
| JP | 2007/059317 A | 3/2007 |
| JP | 2007/059318 A | 3/2007 |
| JP | 2007/222696 A | 9/2007 |
| JP | 2007307440 A | 11/2007 |
| JP | 2007/326013 A | 12/2007 |
| JP | 2008501016 | 1/2008 |
| JP | 2008/302281 A | 12/2008 |
| JP | 2009/183198 A | 8/2009 |
| JP | 2010/111865 A | 5/2010 |
| JP | 2010/184230 A | 8/2010 |
| JP | 2011235262 A | 11/2011 |
| JP | 2011235263 A | 11/2011 |
| JP | 2013103159 A | 5/2013 |
| JP | 2013103160 A | 5/2013 |
| JP | 5213199 B1 | 6/2013 |
| JP | 2013107058 A | 6/2013 |
| JP | 2014099304 A | 5/2014 |
| WO | 1993/014821 A1 | 8/1993 |
| WO | 9314821 | 8/1993 |

(56) References Cited

FOREIGN PATENT DOCUMENTS

| WO | 2004/056471 | A1 | 7/2004 |
|---|---|---|---|
| WO | 2004056468 | A1 | 7/2004 |
| WO | 2004066683 | A1 | 8/2004 |
| WO | 2005/102510 | A1 | 11/2005 |
| WO | 2006/109588 | A1 | 10/2006 |
| WO | 2008073186 | A9 | 6/2008 |
| WO | 2009/110245 | A | 9/2009 |
| WO | 2009/149027 | A2 | 12/2009 |
| WO | 20100013696 | A1 | 2/2010 |
| WO | 2010/087464 | A1 | 8/2010 |
| WO | 2012/002483 | A1 | 1/2012 |
| WO | 2013001629 | A1 | 1/2013 |
| WO | 2013/069779 | A1 | 5/2013 |
| WO | 2013069778 | A1 | 5/2013 |

OTHER PUBLICATIONS

Chinese Office Action dated May 30, 2016 issued in corresponding Chinese Patent Application No. 201580000537.0.
Decision of Rejection dated Aug. 6, 2014 issued in corresponding Japanese Patent Application No. 2014-036728.
International Search Report dated May 26, 2015 issued in corresponding PCT Application No. PCT/JP2015/055336.
Japanese Office Action dated May 2, 2014 issued in corresponding Japanese Patent Application No. 2014-036728.
Chinese Office Action dated Feb. 2, 2015 which issued during prosecution of CN Application No. 201280062762.3.
Chinese Office Action dated Jun. 25, 2015, which issued during prosecution of Chinese Application No. 201180071600.1.
Chinese Office Action dated Mar. 4, 2016, issued in corresponding Application No. 2012800627623.
Chinese Office Action dated Oct. 30, 2014, which issued during prosecution of Chinese Application No. 201180071600.1.
Chinese Office Action dated Sep. 22, 2015 during the prosecution of Chinese Patent Application No. 201280062750.0.
Chinese Office Action dated Sep. 22, 2015 during the prosecution of Chinese Patent Application No. 201280062762.3.
Crespo, et al., "Extraction of Hydrocarbons from Seaweed Samples Using Sonication and Microwave-Assisted Extraction", A Comparative Study Journal of Chromatographic Science, 2006, vol. 44, No. 10, p. 615-618.
Extended European Search Report dated Jul. 13, 2015 which issued during prosecution of EP Application No. 128480480.0.
Extended European Search Report dated Jul. 13, 2015 which issued during prosecution of EP Application No. 12848355.9.
Extended European Search Report dated Jul. 20, 2015 which issued during prosecution of EP Application No. 12848048.0.
Hattab, et al., "Comparison of various extraction methods for identification and determination of volatile metabolites from the brown alga *Dictyopteris membranacea*", Journal of Chromatography A, 2007, vol. 1143, p. 1-7.
Hattab, et al., "Isolation of the Volatile Compounds from the Brown Alga *Dictyopteris membranacea* by Focused Microwave-Assisted Hydrodistillation", J. Essent. Oil Res , 2002, vol. 14, No. 6, p. 422-424.
International Search Report dated Aug. 23, 2011, which issued during the prosecution of International Application No. PCT/JP2011/064965.
International Search Report dated Jan. 29, 2013, from corresponding International Application No. PCT/JP2012/079152.
International Search Report dated Jan. 29, 2013, from corresponding International Application No. PCT/JP2012/079153.
International Search Report dated Sep. 29, 2015 issued in corresponding PCT International Application No. PCT/JP2015/067411.
Shizuka, A. et al., "Microwave Chemical Process: Process Innovation and Application" Fine Chemical, 2011, vol. No 3, pp. 42-46.

Itaya et al., "Effect of Scattering by Fluidization of Electrically Conductive Beads on Electrical Field Intensity Profile in Microwave Dryers" 2005, Drying Technology, 23, p. 273-287.
Japanese Office Action dated Nov. 25, 2015 during the prosecution of Japanese Patent Application No. 2012-522686.
Japanese Office Action, dated Aug. 3, 2011, which issued during the prosecution of Japanese Patent Application No. 2010-111270.
Japanese Office Action, dated Oct. 31, 2013, which issued during the prosecution of Japanese Patent Application No. 2010-111271.
Japanese Search Report dated Jun. 2, 2010, prepared for Japanese Patent Application No. 2010-111271.
Japanese Search Report dated May 31, 2010, prepared for Japanese Patent Application No. 2010-111270.
Notification of Reasons for Rejection dated Aug. 5, 2014 issued in corresponding Japanese Patent Application No. 2014-128981.
Notification of Reasons for Rejection dated Nov. 11, 2014 issued in corresponding Japanese Patent Application No. 2014-128981.
Supplementary European Search Report dated Feb. 26, 2015 which issued during prosecution of EP Application No. 11868832.4.
U.S. Office Action dated Apr. 1, 2015 which issued during prosecution of U.S. Appl. No. 14/357,145.
U.S. Office Action dated Apr. 1, 2015 which issued during prosecution of U.S. Appl. No. 14/357,172.
U.S. Office Action dated Aug. 18, 2015 which issued during prosecution of U.S. Appl. No. 14/357,145.
Written Opinion dated Aug. 23, 2011, which issued during the prosecution of International Application No. PCT/JP2011/064965.
U.S. Office Action dated Aug. 19, 2015 which issued during prosecution of U.S. Appl. No. 14/357,172.
U.S. Office Action dated Jul. 9, 2015 which issued during prosecution of U.S. Appl. No. 13/807,865.
Uy et al., "Seaweed processing using industrial single-mode cavity microwave eating: a preliminary investigation", Carbohydrate Research, 2005, vol. 340, No. 7, p. 1357-1364.
Notification of Result of Substantive Examination issued for Indonesian Patent Application No. P-00201400520 dated Jan. 18, 2019.
Communication issued for European Patent Application No. 11868832.4 dated Feb. 26, 2019.
First Examination Report for Indian Application No. 534/CHENP/2014 dated Nov. 15, 2018.
Office Action for U.S. Appl. No. 13/807,865 dated Nov. 26, 2018.
Communication pursuant to Article 94(3) EPC for European Patent Application No. 12848355.9 dated Dec. 12, 2018.
Office Action for U.S. Appl. No. 14/123,174 dated Jan. 14, 2019.
Technical Examination Report dated Oct. 9, 2018 for Brazilian Patent Application No. 112013033215.
Communication pursuant to Article 94(3) EPC issued in corresponding European Patent Application No. 12 848 048.0 dated Jul. 22, 2019.
Office Action issued in U.S. Appl. No. 14/123,174 dated Jun. 24, 2019.
Final Office Action dated Aug. 7, 2017 during the prosecution of U.S. Appl. No. 14/123,174.
Office Action issued in U.S. Appl. No. 14/123,174 dated Jul. 19, 2018.
Search report issued in Brazilizn Application BR112013033215-8 dated May 18, 2018. with English Translation.
U.S. Office Action (Examiner's Answer) issued in corresponding U.S. Appl. No. 14/123,174 dated Feb. 28, 2020.
Hearing Notice in Reference of Application No. 534/CHENP/2014 issued in corresponding Indian Patent Application dated Dec. 10, 2019.
Summons to attend oral proceedings pursuant to Rule 115(1) EPC issued in corresponding European Patent Application No. 12 848 355 dated Jan. 24, 2020.
Communication pursuant to Article 94(3) EPC issued in corresponding European Patent Application No. 12 848 048.0 dated Oct. 26, 2020.

* cited by examiner

CHEMICAL REACTION METHOD USING CHEMICAL REACTION APPARATUS

CROSS REFERENCE TO RELATED APPLICATIONS

This is a continuation-in-part application of U.S. patent application Ser. No. 15/398,877, filed Jan. 5, 2017, which is a continuation application of U.S. patent application Ser. No. 14/357,145, filed Aug. 26, 2014, now U.S. Pat. No. 9,573, 112 issued Feb. 21, 2017, which is a U.S. National Phase Application under 35 U.S.C. § 371 of International Patent Application No. PCT/JP2012/079152, filed Nov. 9, 2012, which claims priority of Japanese Patent Application No. 2011-247954, filed Nov. 11, 2011. The entire contents of these applications are hereby incorporated by reference.

FIELD OF THE INVENTION

The present invention relates to a chemical reaction method using a chemical reaction apparatus for irradiating microwaves in a reactor.

BACKGROUND

Conventionally, chemical reaction apparatuses and chemical reaction methods are known that perform heat treatment and the like by irradiating a reaction material with microwaves (electromagnetic waves) (see JP 2006-516008A, for example).

SUMMARY OF THE INVENTION

In such conventional chemical reaction apparatuses, there has been a demand for preventing an unreacted content from being discharged.

The present invention was arrived at in view of these circumstances, and it is an object thereof to provide a chemical reaction method using a chemical reaction apparatus capable of preventing an unreacted content from being discharged, by preventing the content from flowing in a shortcut in a horizontal flow-type reactor.

In order to achieve the above-described object, the present invention is directed to a chemical reaction apparatus, including: a horizontal flow-type reactor inside of which has been partitioned into multiple chambers by multiple partition plates, and a liquid content horizontally flows with an unfilled space being provided thereabove; a microwave generator that generates microwaves; and at least one waveguide that transmits the microwaves generated by the microwave generator to the unfilled space in the reactor; wherein the content flows over each of the partition plates, and in each of the chambers, a weir height on an inlet side is higher than a weir height on an outlet side by at least an overflow depth at the partition plate on the outlet side.

With this configuration, at least some of overflows at the respective partition plates do not have the same height. Accordingly, the overflows can be prevented from being directly connected, and a content can be prevented from flowing in a shortcut. As a result, an unreacted content can be prevented from being discharged.

Furthermore, the chemical reaction apparatus of the present invention may be such that the weir heights of the partition plates in the reactor are the same in a state where the reactor is not inclined, and, when the content flows, the reactor is inclined such that, in each of the chambers, the weir height on the inlet side is higher than the weir height on the outlet side by at least the overflow depth at the partition plate on the outlet side.

With this configuration, even in the case where the partition plates have the same weir height, a content can be prevented from flowing in a shortcut by making the reactor inclined.

Furthermore, the chemical reaction apparatus of the present invention may be such that the flow paths have the same shape and are provided in the same number at all of the multiple partition plates, an angle of the inclination is at least $\theta$ that is calculated as: $\theta = \sin^{-1}(H/L)$ (where L is a shortest length of lengths, in a length direction of the reactor, of the respective chambers, and H is an overflow depth obtained using the following equation:

$$15eQ = \sqrt{2g} CN\{4(b-a)H^{5/2} + 10aeH^{3/2}\}$$

where Q is a flow rate, a is a width of a bottom of a trapezoidal flow path, b is a width of an upper side of the trapezoidal flow path, e is a height from the bottom to the upper side of the trapezoidal flow path, C is a flow coefficient, N is a number of the trapezoidal flow paths formed at one partition plate, and g is an acceleration of gravity).

With this configuration, the inclination angle of the reactor can be calculated by determining the flow rate and the shape of the flow path at the partition plates. A content can be prevented from flowing in a shortcut by making the reactor inclined according to this inclination angle.

Furthermore, the chemical reaction apparatus of the present invention may be such that the reactor is not inclined, and, in each of the chambers, a height of a bottom of a flow path at the partition plate on an inlet side is higher than a height of a bottom of a flow path at the partition plate on an outlet side by at least an overflow depth at the partition plate on the outlet side.

With this configuration, even in the case where the reactor is not inclined, a content can be prevented from flowing in a shortcut by setting as appropriate the heights of the flow paths at the partition plates.

Furthermore, the chemical reaction apparatus of the present invention may be such that the overflow depth is H that is calculated using the following equation:

$$15eQ = \sqrt{2g} CN\{4(b-a)H^{5/2} + 10aeH^{3/2}\}$$

(where Q is a flow rate, a is a width of a bottom of a trapezoidal flow path, b is a width of an upper side of the trapezoidal flow path, e is a height from the bottom to the upper side of the trapezoidal flow path, C is a flow coefficient, N is a number of the trapezoidal flow paths formed at one partition plate, and g is an acceleration of gravity).

With this configuration, the overflow depth can be calculated by determining the flow rate and the shape of the flow path at the partition plates, and a difference in the height of the bottom of the flow path between adjacent partition plates can be seen. A content can be prevented from flowing in a shortcut by forming the flow paths at the partition plates according to the difference in the height of the bottom of the flow path between the partition plates.

Furthermore, the chemical reaction apparatus of the present invention may further include at least one agitation unit that rotationally agitates the content inside the reactor.

With this configuration, a content is agitated, and, thus, the content inside the reactor can be more uniformly irradiated with microwaves. As a result, for example, a situation can be avoided in which only part of the content inside the reactor is irradiated with microwaves.

The present invention provides a chemical reaction method using a chemical reaction apparatus capable of preventing an unreacted content from being discharged, by preventing the content from flowing in a shortcut in a horizontal flow-type reactor.

DETAILED DESCRIPTION

Figure 1:
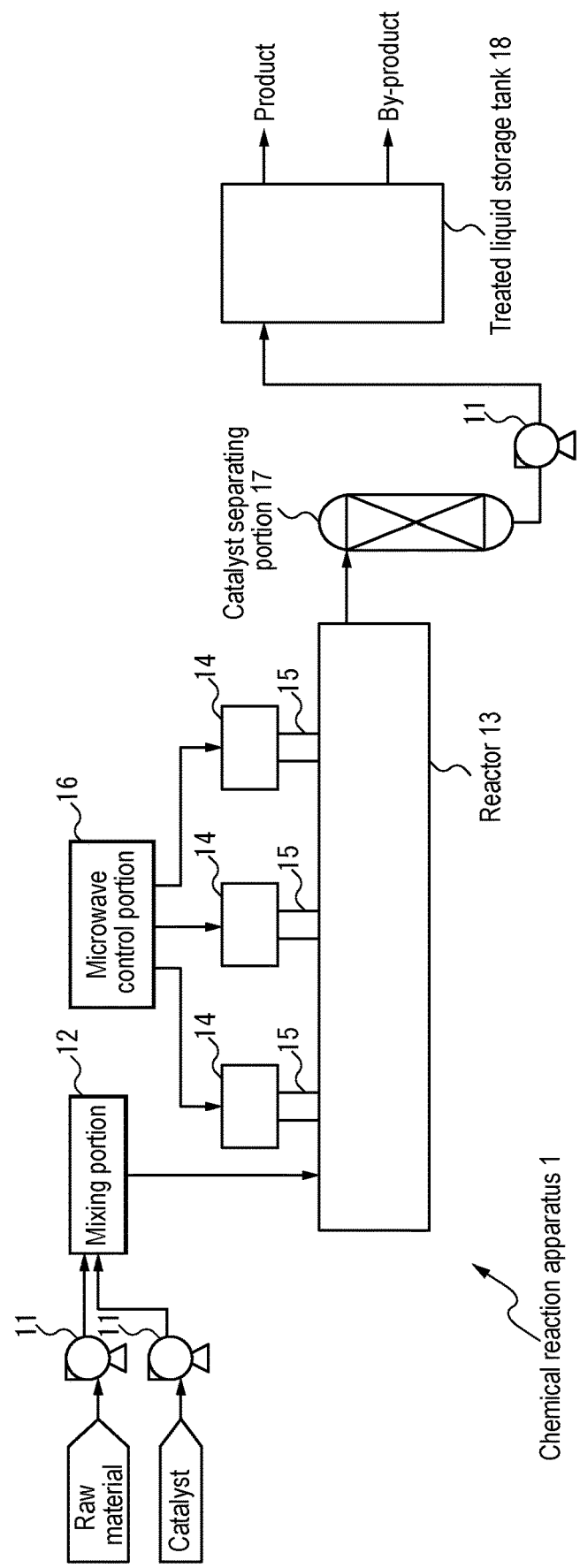
FIG. 1 is a diagram showing the configuration of a chemical reaction apparatus according to Embodiment 1 of the present invention.

Hereinafter, a chemical reaction apparatus according to the present invention will be described by way of an embodiment. Note that constituent elements denoted by the same reference numerals are the same or similar to each other in the following embodiment, and, thus, a description thereof may not be repeated.

Embodiment 1

Below, a chemical reaction apparatus according to Embodiment 1 of the present invention will be described with reference to the drawings. The chemical reaction apparatus according to this embodiment irradiates the content of a reactor with microwaves.

FIG. 1 is a diagram showing the configuration of a chemical reaction apparatus 1 according to this embodiment. The chemical reaction apparatus 1 according to this embodiment includes a mixing portion 12, a reactor 13, microwave generators 14, waveguides 15, a microwave control portion 16, a catalyst separating portion 17, and a treated liquid storage tank 18.

The mixing portion 12 mixes a raw material and a solid catalyst. The mixing portion 12 may mix the raw material and the like with a reactant. The raw material may contain multiple materials. For example, in the case of performing esterification in the reactor 13, fat and oils and alcohol may be used as the raw material. The raw material and the solid catalyst may be supplied to the mixing portion 12 by pumps 11 as shown in FIG. 1, or may be supplied to the mixing portion 12 using other methods. The mixing portion 12 may mix two or more materials, for example, by rotating a blade-like member, a wing-like member, or a screw-like member. Note that, although this embodiment describes the case in which the catalyst that is to be mixed with the raw material is a solid catalyst (heterogeneous catalyst), the catalyst may be a liquid catalyst (homogeneous catalyst). Furthermore, the solid catalyst may or may not form a fluidized bed inside the reactor 13. Furthermore, there is no limitation on the shape of the solid catalyst. Examples of the shape of the solid catalyst include various grains, a cylinder (that may or may not be hollow), a sphere, a pellet, a ring, a shell, and other shapes. Furthermore, the solid catalyst may or may not be, for example, microwave-absorbing or microwave-sensitive. If the solid catalyst is microwave-absorbing or microwave-sensitive, when microwaves are irradiated inside the reactor 13 (described later), the solid catalyst is heated by the microwaves, and the chemical reaction near the solid catalyst is facilitated. Note that the microwave absorptivity and the microwave sensitivity depend on the frequency of microwaves used for irradiation, the temperature inside the reactor 13, and the like. That is to say, materials that have a high dielectric loss factor, at the frequency of microwaves used and the temperature inside the reactor 13 in which the raw material is to undergo a reaction, provide a high microwave absorptivity. Accordingly, for example, a solid catalyst containing such a highly microwave-absorbing material may be used. For example, if microwaves at 2.45 GHz are irradiated, examples of the microwave-absorbing material include carbon except for fullerene (e.g., graphite, carbon nanotube, activated carbon, etc.), iron, nickel, cobalt, ferrite, and the like. Accordingly, the solid catalyst may contain such a microwave-absorbing material. Specifically, the solid catalyst may be a composite in which such a microwave-absorbing or microwave-sensitive material and a metal or metal oxide are combined, a composite in which such a microwave-absorbing or microwave-sensitive material and a catalyst such as alkali catalyst or acid catalyst are combined, or a composite in which a microwave-absorbing or microwave-sensitive material, a catalyst such as alkali catalyst or acid catalyst, and a metal or metal oxide are combined. The composite may be formed, for example, through physical adsorption, chemical bonding, alloying, or other methods. Furthermore, in the mixing portion 12, preliminary heating may or may not be performed for preparation for the reaction in the reactor 13. In the case of performing the preliminary heating, the temperature in the preliminary heating in the mixing portion 12 is preferably controlled such that the raw material and the like at the time of entering the reactor 13 are at a desired temperature or in a desired temperature range. Note that, in the case of not performing the preliminary heating in the mixing portion 12, heating corresponding to the preliminary heating may be performed in the reactor 13. The raw material and the solid catalyst mixed by the mixing portion 12 are loaded into the upstream side in the reactor 13.

The reactor 13 is a horizontal flow-type reaction unit in which a liquid content horizontally flows with an unfilled space being provided thereabove. The reactor 13 in which the content horizontally flows refers to a reactor that is not a vertical flow-type reaction unit in which the content vertically flows, that is, the content does not have to strictly horizontally flow. It is sufficient that the content flows in a direction close to the horizontal direction on the whole. Examples of the content include a mixture of the raw material and the catalyst. The raw material and the catalyst mixed by the mixing portion 12 flow inside the reactor 13. Note that, since the chemical reaction in the reactor 13 produces a product material from the raw material, the content of the reactor 13 may be considered to contain the product material. That is to say, the content may be referred to as the raw material and/or the product material. Furthermore, since an unfilled space is present above the content, the content is typically a material other than gas. Furthermore, the content can flow inside the reactor 13 and has a flat liquid surface, and, thus, the content is a material other than solid (e.g., powders or grains, etc.). Accordingly, the content is liquid. The liquid content may be for example, a material having a high flowability such as water, oil, aqueous solution, or colloidal solution, or may be a material having a low flowability such as slurry or suspension. It is preferable that the liquid surface of the content inside the reactor 13 is kept horizontal, and, thus, even in the case where the flowability of the liquid content is low, it preferably allows the liquid surface to be horizontal after a while without the application of vibration from the outside. That is to say, the liquid content preferably has a flowability that allows the shape of the surface to be changed without vibration from the outside. Note that the liquid surface being horizontal may refer to the state of being completely flat, or may refer to the state of being flat on the whole although there are slightly rough portions. The reason for this is that, if the content does not have a high flowability, the liquid surface may not be completely flat. The inner wall of the reactor 13 is preferably made of a microwave-reflecting material. Examples of the microwave-reflecting material include metal. The internal configuration of the reactor 13 will be described later.

The microwave generators 14 generate microwaves. The chemical reaction apparatus 1 according to this embodiment may include one microwave generator 14, or may include two or more microwave generators 14. There is no limitation on the frequency of the microwaves, and examples thereof include 2.45 GHz, 5.8 GHz, 24 GHz, 913 MHz, and other frequencies ranging from 300 MHz to 300 GHz.

The one or more waveguides 15 transmit the microwaves generated by the microwave generators 14 to the unfilled space in the reactor 13. The number of waveguides 15 provided may be the same as the number of microwave generators 14 as shown in FIG. 1. Furthermore, the waveguide 15 may be branched and transmit the microwaves to two or more positions in the unfilled space. Note that the specification of the waveguides 15 is preferably in accordance with the frequency of the microwaves generated by the microwave generators 14.

The microwave control portion 16 controls the power of microwaves used for irradiation in the reactor 13, according to the temperature measured by temperature measuring portions 25 (described later). The control by the microwave control portion 16 makes it possible to keep inside the reactor 13 at a desired temperature or in a desired temperature range.

The catalyst separating portion 17 separates the catalyst from the product material after the reaction in the reactor 13. If the catalyst that has been mixed with the raw material is a solid catalyst, for example, filtering may be used to separate the solid catalyst, or one of the solid catalyst and the product material may be precipitated to separate the solid catalyst. Furthermore, if the solid catalyst contains a magnetic substance, a magnet (that may be a permanent magnet or may be an electromagnet) for attracting the solid catalyst may be used to separate the solid catalyst. Note that the separated solid catalyst may be used again as appropriate. Furthermore, if a liquid catalyst is used, distillation, extraction, or neutralization may be performed in the catalyst separating portion 17 to separate the catalyst.

The product material from which the catalyst has been separated by the catalyst separating portion 17 is loaded into the treated liquid storage tank 18. Then, this product material is separated as appropriate into a final product, a by-product, and the like. For example, if the raw material is free fatty acid, and esterification is performed in the reactor 13, a product that is biodiesel fuel and a by-product that is water are obtained. In this case, an acid catalyst is used. Furthermore, for example, if the raw material is triglyceride, and transesterification is performed in the reactor 13, a product that is biodiesel fuel and a by-product that is glycerin are obtained. In this case, an alkali catalyst is used.

Note that an unshown cooler that cools down the material after the reaction in the reactor 13 may or may not be provided on the path after the reactor 13. In the former case, for example, the cooler may use water to cool down the material after the reaction in the reactor 13.

Figure 2:
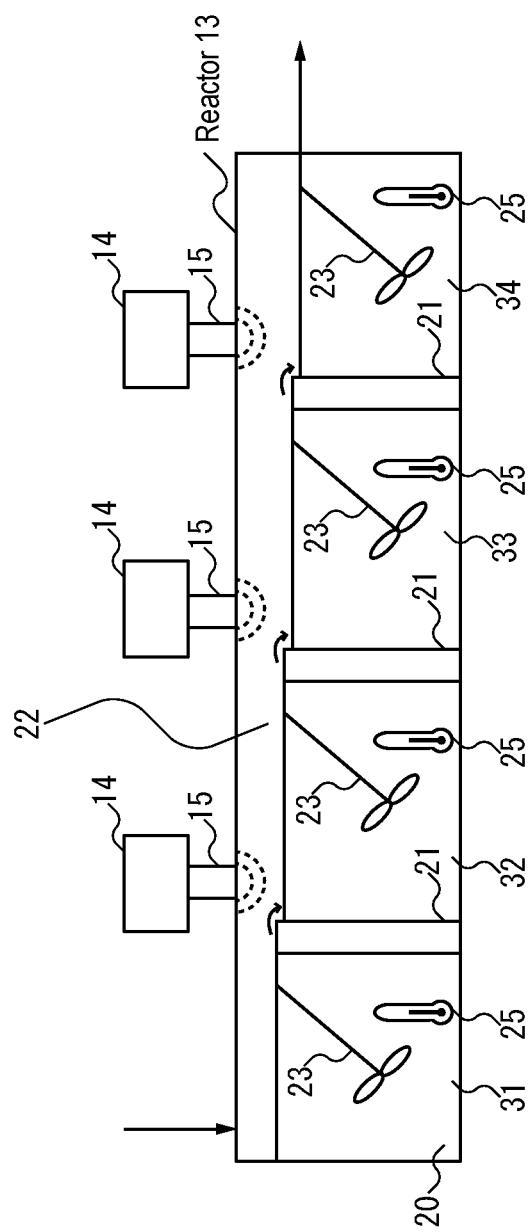
FIG. 2 is a view showing an exemplary internal configuration of a reactor according to the embodiment.

FIG. 2 is a view showing an exemplary internal structure of the reactor 13 according to this embodiment. In FIG. 2, the inside of the reactor 13 is partitioned by multiple partition plates 21 into multiple chambers 31, 32, 33, and 34. The multiple chambers 31, 32, 33, and 34 are chambers that are continuously arranged in series. As described above, an unfilled space 22 is present in the upper portion inside the reactor 13. The unfilled space 22 is irradiated with the microwaves generated by the microwave generators 14 and transmitted via the waveguides 15. Note that FIG. 2 shows the case in which a single unfilled space is present inside the reactor 13, that is, the case in which an unfilled space is shared by all the chambers 31 to 34, but there is no limitation to this. That is to say, an unfilled space may be shared by at least two or more chambers that are part of all chambers, or may be shared by none of the chambers (in this case, there are unfilled spaces that have been separated from each other by the partition plates 21). The waveguides 15 may or may not be provided respectively at the upstream positions in the chambers 32, 33, and 34 as shown in FIG. 2. In the former case, for example, the microwaves that have been transmitted by one waveguide 15 to the unfilled space 22 are mainly irradiated on the chamber present therebelow. Since microwaves are transmitted through an unfilled space, for example, the microwaves that have been transmitted by the waveguide 15 at the position of the chamber 32 are irradiated via the unfilled space also on the content in the chamber 31 and the chamber 33. Note that the waveguides 15 may be provided at the positions of the partition plates 21, that is, at the positions above the partition plates 21. Accordingly, the microwaves that have been transmitted by one waveguide 15 to the unfilled space 22 are mainly irradiated on two chambers that have been partitioned from each other by the partition plate 21 at the position corresponding to that waveguide 15. If the unfilled space 22 is shared by multiple chambers, the microwaves that have been transmitted to the shared unfilled space 22 are irradiated on a content 20 in the multiple chambers sharing the unfilled space 22. The partition plates 21 may transmit microwaves, may absorb microwaves, or may reflect microwaves. Examples of the microwave-transmitting material include Teflon (registered trademark), quartz glass, ceramic, silicon nitride-alumina, and the like. Accordingly, the partition plates 21 that transmit microwaves may be made of such a microwave-transmitting material. Furthermore, examples of the microwave-absorbing material include carbon except for fullerene, and the like. Accordingly, the partition plates 21 that absorb microwaves may be made of such a microwave-absorbing material. Furthermore, examples of the microwave-reflecting material include metal. Accordingly, the partition plates 21 that do not transmit microwaves may be made of such a microwave-reflecting material. Furthermore, the partition plates 21 may be made of a combination of two or more freely selected from the microwave-transmitting material, the microwave-absorbing material, and the microwave-reflecting material.

Furthermore, as shown in FIG. 2, the chemical reaction apparatus 1 may further include agitation units 23. That is to say, the chemical reaction apparatus 1 according to this embodiment may include one or more agitation units 23 that rotationally agitate the content 20 inside the reactor 13. FIG. 2 shows the case in which the chambers 31 to 34 respectively have the agitation units 23, but there is no limitation to this. One or more chambers may not have the agitation unit 23. Furthermore, FIG. 2 shows the case in which each of the agitation units 23 is in the shape of a blade, but this merely schematically shows the agitation units 23. The agitation may be performed, for example, by rotating a blade-like, wing-like, or rod-like rotatable member. The rotatable member may be made of a microwave-transmitting material, a microwave-absorbing material, a microwave-reflecting material, or a combination of two or more freely selected from the microwave-transmitting material, the microwave-absorbing material, and the microwave-reflecting material. The rotation may be performed, for example, by rotating a rotatable member attached to a shaft in accordance with the rotation of the shaft, or by rotating the rotatable member using a magnetic force as in the case of a magnetic stirrer. In the former case, the shaft may be provided independently for each chamber, or may be shared by multiple chambers. In the latter case, the rotatable member (magnetic stirrer) in the shape of a rod, a blade, a wing, or the like is rotated by a magnet. The agitation of the content by the agitation units 23 may be used to cause the content to flow from the upstream side to the downstream side, or in the opposite direction, but there is no limitation to this. Note that rotational agitation is already known, and, thus, a detailed description thereof has been omitted.

Hereinafter, reasons why the content of the reactor 13 is rotationally agitated by the agitation units 23 will be briefly described. A first reason why the content is agitated by the agitation units 23 is to uniformly heat the content with microwaves. Although depending on the type of content and the temperature of the content, the depth to which microwaves penetrate is fixed, and, thus, the agitation is performed in order to uniformly irradiate and uniformly heat the entire content with microwaves. Furthermore, the content can be more efficiently irradiated with microwaves as the surface area of the content at the unfilled space 22 increases. Accordingly, a second reason why the content is agitated is to increase the area subjected to microwave irradiation. Thus, the content is agitated by the agitation units 23 preferably at an intensity that allows the surface of the content at the unfilled space 22 to be disordered, but there is no limitation to this (if the agitation is performed for the first reason, it may be sufficient that the entire content is eventually heated). Furthermore, since the raw material and the like are agitated using the agitation units 23 in this manner, even in the case where a raw material contains two or more materials having different densities, these materials can be mixed and reacted with each other as appropriate. For example, when causing materials having different densities, such as alcohol and waste oil, to react with each other in a vertical flow-type reactor, these materials are easily separated from each other. However, as in this embodiment, if the reactor 13 is of a horizontal flow-type and is provided with the agitation units 23, these materials can be mixed and reacted with each other as appropriate.

Furthermore, as shown in FIG. 2, the reactor 13 also may have the temperature measuring portions 25. That is to say, the chemical reaction apparatus 1 according to this embodiment may have the temperature measuring portions 25 that measure the temperature inside the reactor 13. The temperature inside the reactor 13 is preferably the temperature of the content of the reactor 13. FIG. 2 schematically shows the case in which the chambers 31 to 34 respectively have the temperature measuring portions 25, but there is no limitation to this. One or more chambers may not have the temperature measuring portion 25. Furthermore, FIG. 2 merely schematically shows the temperature measuring portions 25. The temperature measuring portions 25 may measure the temperature, for example, using a thermocouple, an infrared sensor, an optical fiber, or other methods. The temperature measured by the temperature measuring portions 25 (strictly speaking, data indicating the temperature) is passed to the microwave control portion 16, and is used to control the power of microwaves from the microwave generators 14. As described above, this control may be control for keeping the temperature of the chambers 31 to 34 at a desired temperature or in a desired temperature range. For example, if microwaves are irradiated on the position of each partition plate 21, the power of microwaves irradiated on that position may be controlled, for example, using one or both of the temperatures of two chambers that have been partitioned from each other by the partition plate 21 at the position subjected to the microwave irradiation. In the former case, for example, the control may be performed using a lower temperature, using a higher temperature, or using a temperature of a chamber specified in advance. In the latter case, for example, the control may be performed using an average of these temperatures, or using a weighted average according to the capacities of both chambers (average in consideration of weights according to the capacities of the chambers).

Furthermore, the wall face of the reactor 13 may be covered by a heat insulating material. In that case, heat inside the reactor 13 can be prevented from being dissipated to the outside.

Figure 3A:
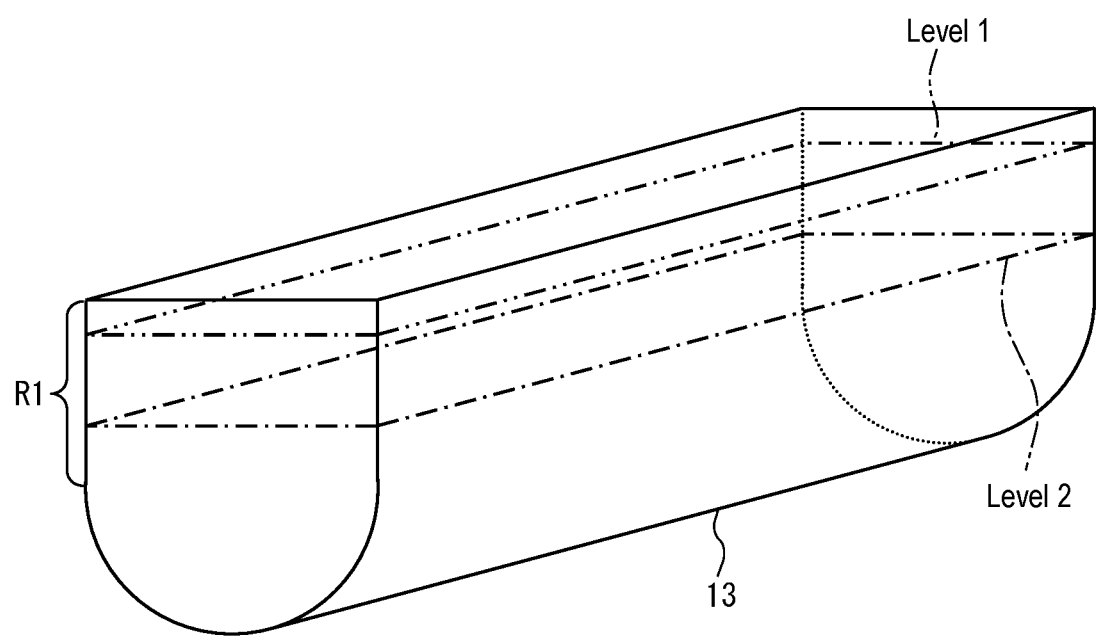
FIG. 3A is a perspective view showing an exemplary shape of the reactor according to the embodiment.
Figure 3B:
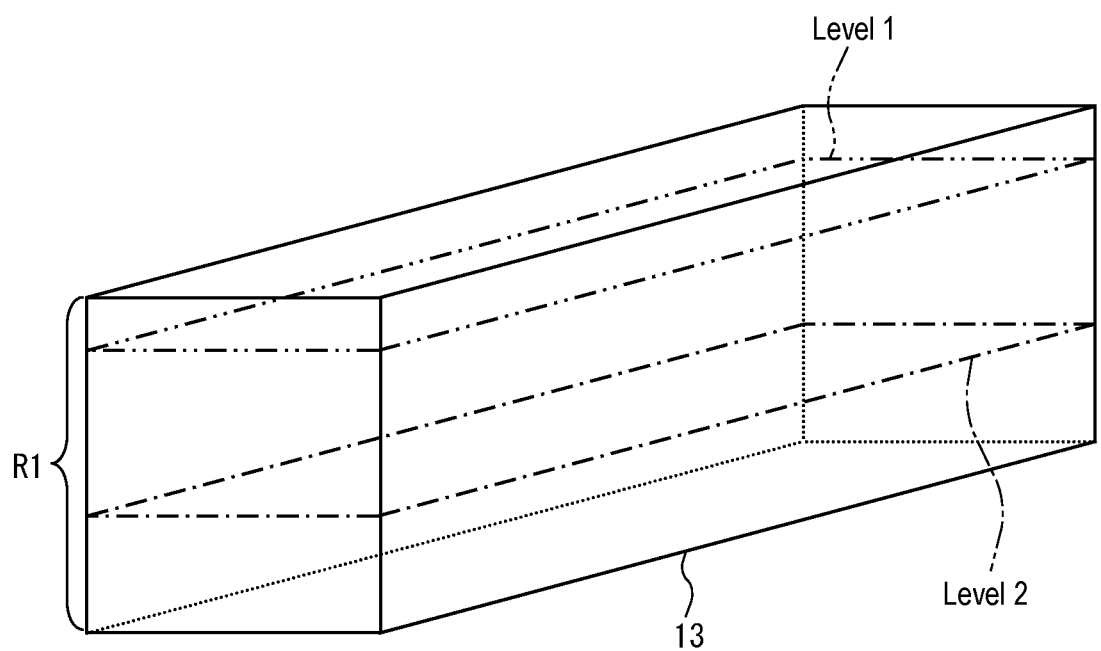
FIG. 3B is a perspective view showing an exemplary shape of the reactor according to the embodiment.

FIGS. 3A and 3B are views showing an exemplary shape of the reactor 13 according to this embodiment. In FIGS. 3A and 3B, the partition plates 21, the agitation units 23, and the like have been omitted for the sake of convenience of the description. In FIGS. 3A and 3B, the reactor 13 according to this embodiment has a shape in which the area of the liquid surface does not change even in the case where the height of the liquid surface changes according to a change in the amount of the content. Note that "the area of the liquid surface does not change even in the case where the height of the liquid surface changes according to a change in the amount of the content" refers to that there is at least the range of the content within which the area of the liquid surface does not change even in the case where the amount of the content changes. Accordingly, it is conceivable that the area of the liquid surface does not change according to the amount of the content regardless of the amount of the content, or that the area of the liquid surface does not change according to the amount of the content as long as the amount of the content is within a predetermined range, that is, as long as the amount of the content is between a first amount and a second amount (assuming that the second amount is larger than the first amount). In this embodiment, the latter case will be mainly described. That is to say, in this embodiment, the reactor 13 has a shape in which the area of the liquid surface does not change according to a change in the amount of the content as long as the amount of the content is within a predetermined range. Accordingly, the reactor 13 may have a shape in which the cross-section in the liquid surface direction of the content does not change as long as the amount of the content is within a predetermined range, for example, as shown in FIGS. 3A and 3B. In this case, within the range of the height of the liquid surface when the amount of the content changes from the first amount to the second amount, the shape in the horizontal direction inside the reactor 13 corresponding to the height of the liquid surface does not change. Note that the above-described first amount is typically the lower limit value of the content in the case where the area of the liquid surface does not change, and the second amount is typically the upper limit value of the content in the case where the area of the liquid surface does not change. Furthermore, even when the content is at the second amount, an unfilled space has to be present above the content. The reason for this is that microwaves are irradiated via an unfilled space in the reactor 13. Furthermore, the liquid surface may be disordered when agitation is performed inside the reactor 13 as described above, but the liquid surface described here is the liquid surface without such disorder or the like. Note that "the height of the liquid surface" is the height of the liquid surface in the vertical direction.

In FIG. 3A, the reactor 13 has a semicylindrical shape elongated in the flow direction and projecting downward. That is to say, the reactor 13 in FIG. 3A has a shape in which an open-topped semicylinder projecting downward and an open-bottomed rectangular solid having the same length as the semicylinder are joined at their openings. Note that the opening of the semicylinder and the opening of the rectangular solid have the same size and the same shape, and they are joined at their openings to form the reactor 13. In other words, the reactor 13 in FIG. 3A has a hollow shape having a side face with a U-shaped cross-section and an upper face with a cross-section closing the opening of the U-shape, wherein the openings at both ends of the hollow shape are closed by flat faces perpendicular to the length direction. In the reactor 13 in FIG. 3A, the area of the liquid surface does not change as long as the height of the liquid surface of the content is within a range R1 (e.g., the heights at a level 1, at a level 2, etc.). Note that the height of the liquid surface at the lowest level in the range R1 corresponds to the lowest position in the rectangular solid forming the upper portion of the reactor 13.

In FIG. 3B, the reactor 13 is in the shape of a rectangular solid. In the reactor 13 in FIG. 3B, the area of the liquid surface does not change as long as the height of the liquid surface of the content is within the range R1, which covers the entire height (e.g., the heights at the level 1, at the level 2, etc.). That is to say, the area of the liquid surface does not change regardless of the amount of the content.

Figure 4A:
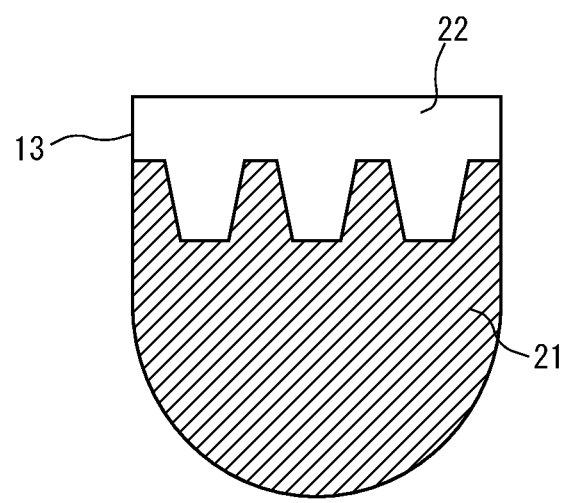
FIG. 4A is a view showing an exemplary shape of a partition plate according to the embodiment.
Figure 4B:
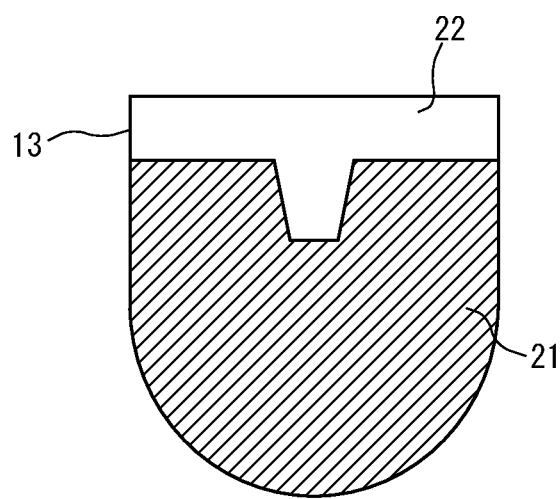
FIG. 4B is a view showing an exemplary shape of the partition plate according to the embodiment.
Figure 5A:
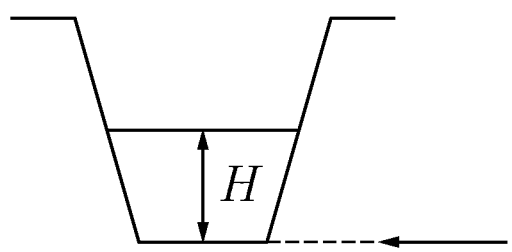
FIG. 5A is a view showing an exemplary shape of a flow path according to the embodiment.
Figure 5B:
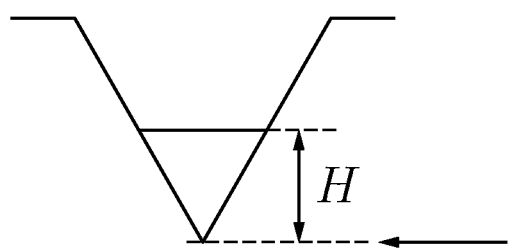
FIG. 5B is a view showing an exemplary shape of the flow path according to the embodiment.
Figure 5C:
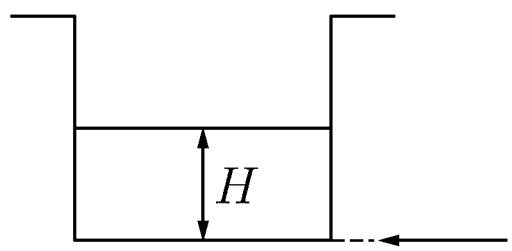
FIG. 5C is a view showing an exemplary shape of the flow path according to the embodiment.

Next, the partition plates 21 will be described. The content 20 such as a raw material loaded into the reactor 13 flows through the chambers 31 to 34 and is finally discharged from the downstream side (the right end of the reactor 13 in FIG. 2). Note that a flow path that allows the content to flow is formed at the partition plates 21. In this embodiment, the flow path is an overflow-type flow path formed above the partition plates 21. That is to say, in this embodiment, the content flows over each of the partition plates 21. The flow path allows the content to flow from the upstream side (the left side in FIG. 2) to the downstream side (the right side in FIG. 2) in the reactor 13. FIGS. 4A and 4B are views showing the partition plate 21 provided in the reactor 13 in the shape as shown in FIG. 3A, in the length direction of the reactor 13. The partition plate 21 does not extend to the position of the unfilled space 22, and the content flows through that position (that is, over the partition plate 21). The number of overflow-type flow paths may be three as shown in FIG. 4A, may be one as shown in FIG. 4B, or may be other numbers (two, or four or more). Furthermore, each flow path may be trapezoidal as shown in FIGS. 4A, 4B, and 5A, may be V-shaped as shown in FIG. 5B (wedge-shaped), may be quadrangular (rectangular) as shown in FIG. 5C, or may be in other shapes (e.g., U-shaped, semicircular, etc.). If the partition plate 21 has multiple flow paths, the flow paths may have different shapes, or may have the same shape. Furthermore, if the partition plate 21 has multiple flow paths, the bottoms of the flow paths (the lowest points of the flow paths) preferably have the same height. The height position of the bottom of a flow path may be referred to as a "weir height". In FIGS. 5A to 5C, the position indicated by the left-pointing arrow is the weir height (the height position of the bottom of a flow path). The weir height indicates the height in the vertical direction. Furthermore, if the flow path is rectangular, the width of the flow path may be the same as the width of the reactor 13. That is to say, the partition plate 21 in that case has, on the upper side thereof, no recess such as cutout (portion that has been cut out), and a flow path is formed throughout the width of the reactor 13 (full-width weir). Although FIGS. 4A and 4B each show a partition plate in the case where the unfilled space 22 is shared by two chambers that have been partitioned from each other by that partition plate 21, the partition plate 21 may extend also to the position of the unfilled space 22, in the case where the unfilled space 22 is not shared. For example, in the partition plate 21 in FIGS. 4A and 4B, the partition plate may extend to above the upper side of the trapezoidal flow path. That is to say, the partition plate 21 may have multiple trapezoidal holes in accordance with flow paths. Also in that case, in the flow paths respectively formed by the holes, the content may be regarded as flowing over the partition plate 21. It will be appreciated that, if the reactor 13 has a shape other than that in FIG. 3A, the partition plate 21 is shaped in accordance with that shape of the reactor 13. Furthermore, if there are multiple partition plates 21 inside the reactor 13, the partition plates 21 may have the same shape, or may have different shapes. Furthermore, the partition plate 21 has a thickness of, for example, approximately 1 to 20 mm, which is sufficiently smaller than the length of each chamber (the length in the length direction of the reactor 13).

Figure 6A:
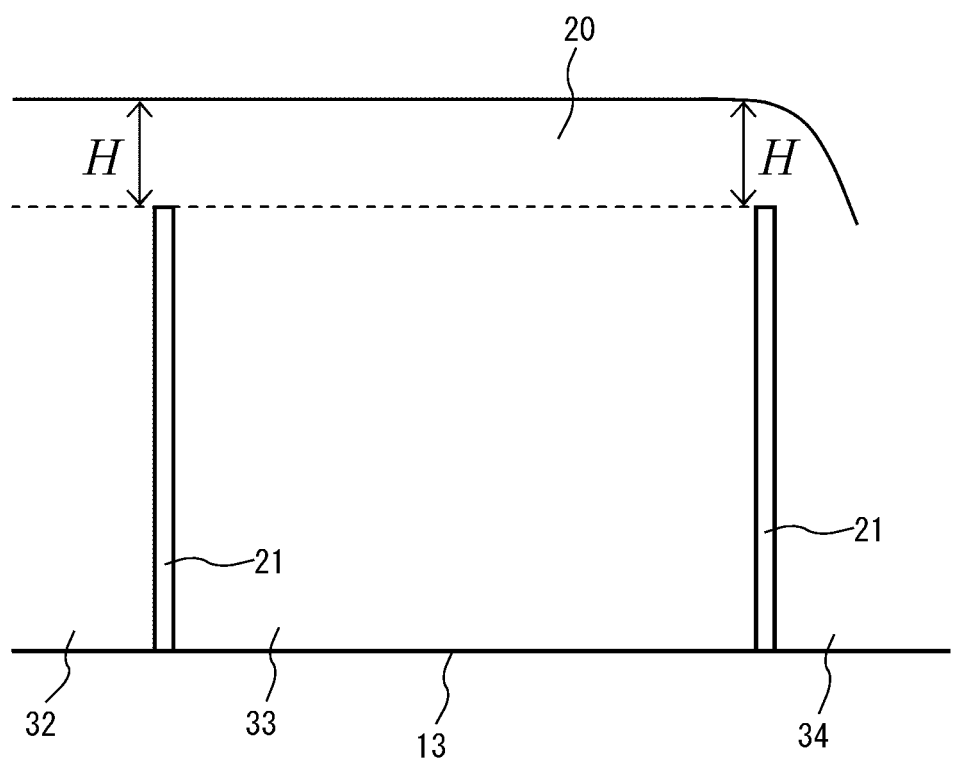
FIG. 6A is a view illustrating a relationship between the partition plates and overflows according to the embodiment.
Figure 6B:
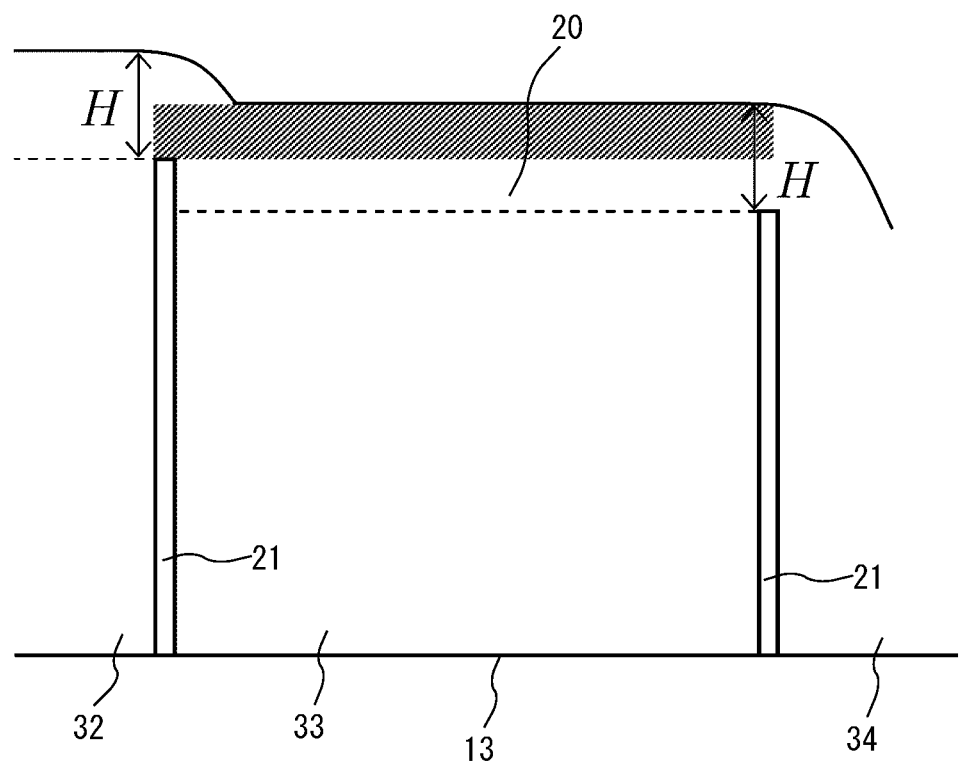
FIG. 6B is a view illustrating a relationship between the partition plates and overflows according to the embodiment.
Figure 6C:
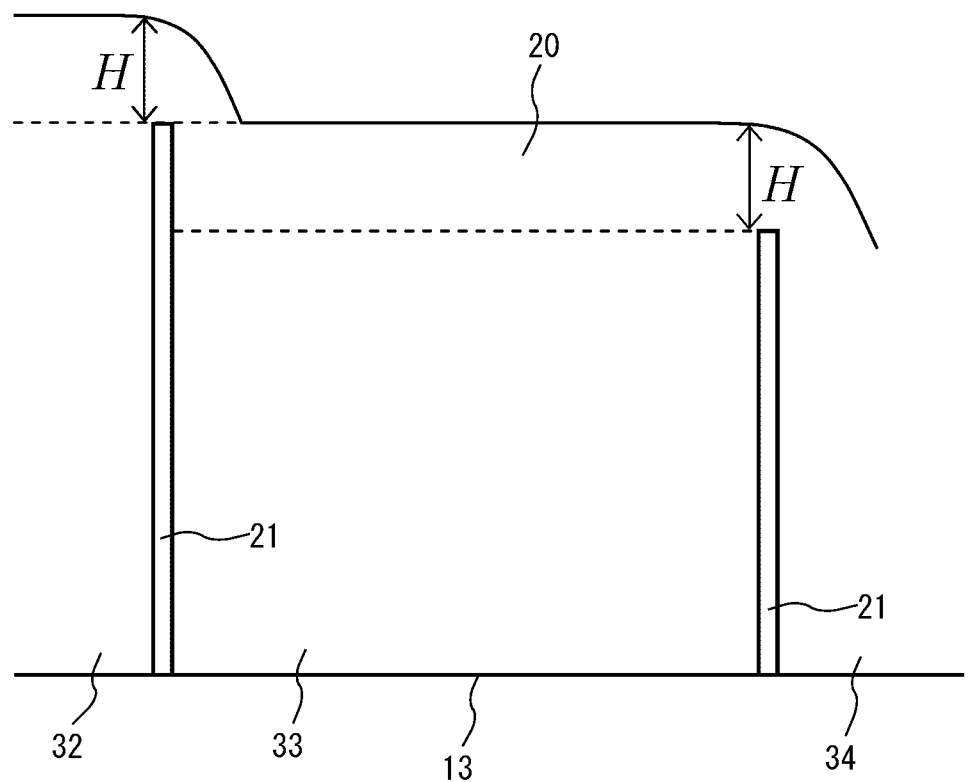
FIG. 6C is a view illustrating a relationship between the partition plates and overflows according to the embodiment.

(1) The Case in which the Reactor is not Inclined and there is a Height Difference Between the Partition Plates Next, the weir heights of the partition plates 21 in the case where the reactor 13 is not inclined will be described. In this case, a description will be made focusing on the chamber 33, but the same is applicable to the other chambers. As shown by the partition plate 21 on the right side in FIG. 6A, in an overflow-type flow path, the height of the content 20 is higher than the weir height of the partition plate 21 by an overflow depth H. The overflow depth is the height of an overflow when the content flows through the flow path over the partition plate 21, that is, the height from the weir height to the highest position in the content (the height in the vertical direction). In FIGS. 5A to 5C, the overflow depth is indicated by H. Furthermore, in the case as shown in FIG. 6A where the reactor 13 is not inclined and the partition plate 21 on the inlet side (the left side in the drawing) of the chamber 33 and the partition plate 21 on the outlet side (the right side in the drawing) have the same weir height, the partition plate 21 on the inlet side of the chamber 33 and the partition plate 21 on the outlet side have the same overflow height, and the overflows at the partition plates 21 are directly connected in the left-right direction. Accordingly, at least part of the content 20 may move from the chamber 32 to the chamber 34 without being retained in the chamber 33 due to the directly connected overflows. That is to say, in the case of FIG. 6A, the content 20 may flow in a shortcut and be discharged from the chamber 33. Furthermore, also in the case as shown in FIG. 6B where the weir height of the partition plate 21 on the inlet side of the chamber 33 is higher than the weir height of the partition plate 21 on the outlet side but at least part (shaded portion in the drawing) of the overflows at the partition plates 21 are directly connected in the left-right direction, at least part of the content 20 may flow in a shortcut without being retained in the chamber 33 due to the directly connected overflows. On the other hand, in the case as shown in FIG. 6C where the weir height of the partition plate 21 on the inlet side of the chamber 33 is higher than the weir height of the partition plate 21 on the outlet side by the overflow depth H on the outlet side, the overflows at the partition plates 21 are not directly connected in any portion in the left-right direction. In this case, when the content 20 flows into chamber 33 over the partition plate 21 on the inlet side, all the content 20 moves at least downward. Thus, according to a decrease in the potential energy due to that movement, the content 20 that has flown into the chamber 33 sinks toward the bottom of the chamber 33. Accordingly, in the case of FIG. 6C, the content 20 that has flown into the chamber 33 via the overflow on the inlet side hardly flows out as it is via the overflow on the outlet side, compared with the cases of FIGS. 6A and 6B. Thus, it seems that the content 20 can be effectively prevented from flowing in a shortcut. Accordingly, it is sufficient that, in each chamber of the reactor 13, the weir height on the inlet side is higher than the weir height on the outlet side by at least the overflow depth H at the partition plate 21 on the outlet side. Accordingly, the content 20 can be prevented from flowing in a shortcut in each chamber. In order to achieve this, as described in FIG. 6C, the partition plates 21 may be used in which the height of the bottom of the flow path (weir height) at the partition plate 21 on the inlet side is higher than the height of the bottom of the flow path (weir height) at the partition plate 21 on the outlet side by at least the overflow depth H at the partition plate 21 on the outlet side, in each chamber of the reactor 13 that is not inclined. Furthermore, as described later, the weir height on the inlet side may be made higher than the weir height on the outlet side by at least the overflow depth H at the partition plate 21 on the outlet side in each chamber of the reactor 13, by making the reactor 13 inclined. Furthermore, if the weir height of the partition plate 21 on the inlet side of the chamber 33 is higher than the weir height of the partition plate 21 on the outlet side by the overflow depth H on the outlet side in this manner, a reversed flow also can be prevented. Note that, in FIGS. 6A to 6C, the agitation units 23 and the temperature measuring portions 25 have been omitted for the sake of convenience of the description. Furthermore, portions of the partition plates 21 above the weir height also have been omitted for the sake of convenience of the description.

Figure 7:
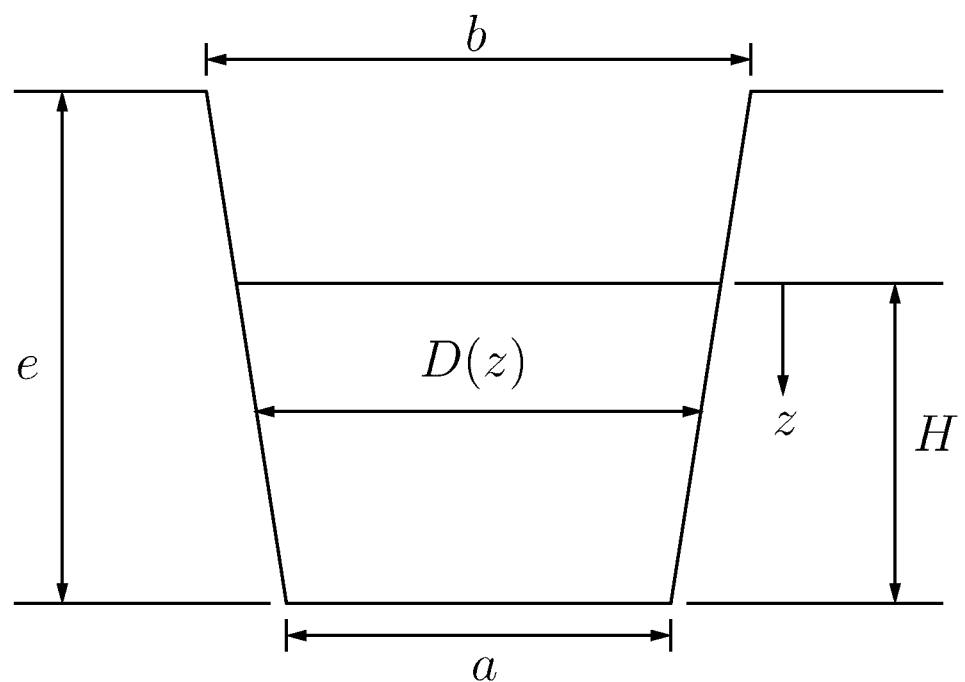
FIG. 7 is a view showing a trapezoidal flow path according to the embodiment.

Next, the overflow depth H will be described. Below, a case will be described in which the partition plate 21 has N trapezoidal flow paths shown in FIG. 7. It is assumed that the N flow paths have the same shape and the same weir height. Note that, in the trapezoidal flow path in FIG. 7, if a width a of the bottom of the trapezoidal flow path is equal to a width b of the upper side, that is, if a=b, the flow path is rectangular. Furthermore, if the width a of the bottom of the trapezoidal flow path is 0, that is, if a=0, the flow path is V-shaped. Note that the height of the trapezoidal flow path is taken as e, and the z axis is set vertically downward from the upper face of the overflow. In this case, D(z) is represented by the following equation.

$$D(z) = -\frac{b-a}{e}z + \frac{b-a}{e}H + a$$

Using Bernoulli's theorem $v=(2gz)^{1/2}$, a flow rate Q is represented by the following equation. In the equation, g is an acceleration of gravity, C is a flow coefficient, and v is a fluid velocity. The flow coefficient is determined according to the shape of the flow path, and, for example, may be calculated by experiment, or may be calculated by computation.

$$Q = \int_0^H CND(z)\sqrt{2gz}\,dz$$

If D(z) above is substituted for this equation and integration is performed with z, the following equation is obtained.

$$Q = \frac{CN\sqrt{2g}}{15e}\{4(b-a)H^{5/2} + 10aeH^{3/2}\}$$

This equation can be rewritten as follows.

$$15eQ = \sqrt{2g}CN\{4(b-a)H^{5/2} + 10aeH^{3/2}\}$$

The overflow depth H can be calculated by solving this equation. Furthermore, if the flow paths are provided in the same number and have the same shape at the partition plates in the reactor 13, the partition plates 21 have the same overflow depth H. Accordingly, if the partition plates 21 are designed such that the height of the bottom of the flow path (weir height) at the partition plate 21 on the inlet side is higher than the height of the bottom of the flow path (weir height) at its adjacent partition plate 21 on the outlet side by at least the overflow depth H, the content can be prevented from flowing in a shortcut in the reactor 13, and, thus, an unreacted content can be prevented from being discharged out of the reactor 13.

It is preferable that the height of an outlet in the last chamber 34 has the same relationship as that of the weir height described above. That is to say, it is preferable that, in the last chamber 34, the height of the bottom of the flow path (weir height) at the partition plate 21 on the inlet side is higher than the height of the bottom of the flow path at the outlet by at least the overflow depth at the outlet. The shape of a flow path at the partition plates 21 is typically different from the shape of the outlet in the last chamber 34, and, thus, the overflow depth at the outlet may be computed separately from the overflow depth H at the partition plates 21. The overflow depth of a trapezoidal flow path can be calculated using D(z) above, and the overflow depth of a flow path in the other shapes can be calculated using D(z) according to that shape as appropriate and performing integration thereon.

Furthermore, in the case of (1), the flow paths may have different shapes and be provided in different numbers at the multiple partition plates 21. In that case, the overflow depth Hi is calculated for each of the partition plates 21. Here, i is an index (an integer of one or more) for identifying the partition plates 21. It is sufficient that, in each chamber, the weir height on the inlet side is higher than the weir height on the outlet side by at least the overflow depth Hi at the partition plate 21 on the outlet side.

Figure 8:
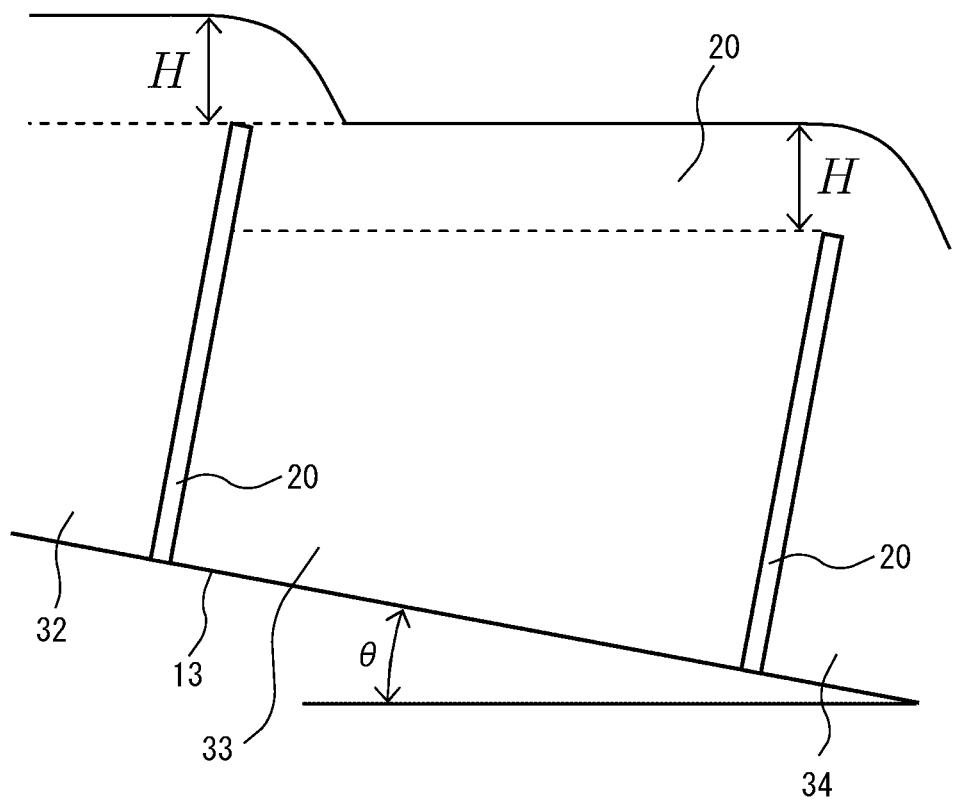
FIG. 8 is a view illustrating a relationship between the partition plates and overflows according to the embodiment.

(2) The Case in which the Reactor is Inclined and there is No Height Difference Between the Partition Plates Next, the case will be described in which the reactor 13 is inclined to realize the same effects as in the case where a height difference is provided between the partition plates 21. It is assumed that the weir heights of the partition plates 21 are the same in the case where the reactor 13 is not inclined. Furthermore, the flow paths have the same shape and are provided in the same number at all of the multiple partition plates 21. That is to say, if the cross-sections inside the reactor 13 in a direction orthogonal to the length direction of the reactor 13 do not change, all the partition plates 21 may have the same shape. Also in this case, if the reactor 13 is inclined such that the weir height on the inlet side is higher than the weir height on the outlet side by at least the overflow depth at the partition plate 21 on the outlet side in each chamber as shown in FIG. 8 when the content 20 flows, that is, when the content 20 is treated, the same effects can be realized as in the case where a height difference is provided between the partition plates 21 as described above. It will be appreciated that the reactor 13 is inclined such that the inlet side of the content is positioned on the upper side and the outlet side is positioned on the lower side.

Figure 9:
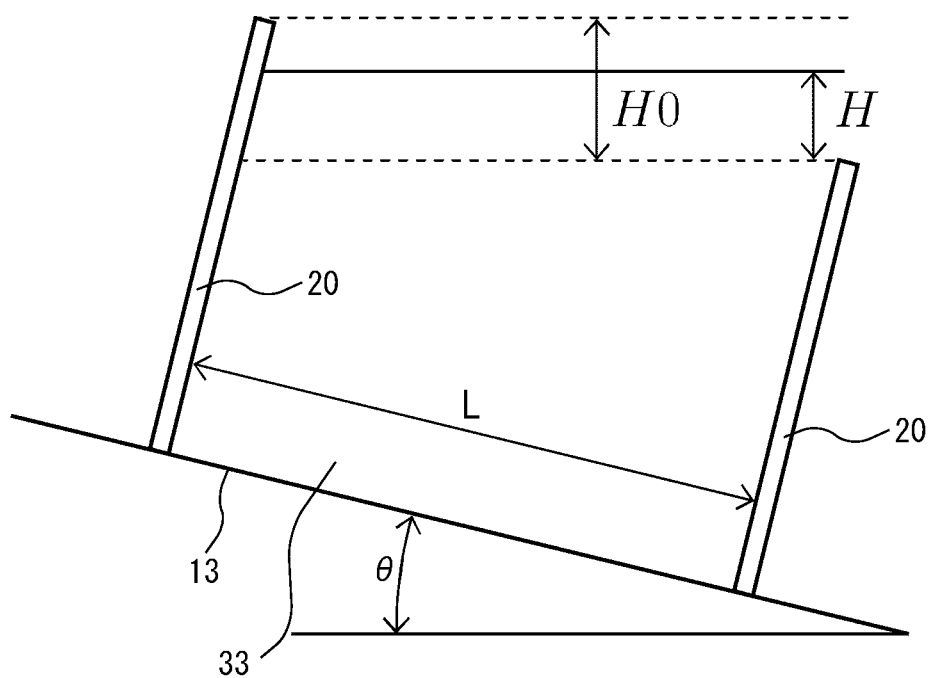
FIG. 9 is a view illustrating a relationship between an overflow depth, an inclination angle, and the like according to the embodiment.

Hereinafter, an inclination angle in the case where the reactor 13 is inclined will be described. As shown in FIG. 9, the length of the chamber 33 in the length direction of the reactor 13 is taken as L. Although there is no limitation on length L, it is, for example, approximately 10 to 300 cm, preferably approximately 10 to 100 cm. Furthermore, it is assumed that the reactor 13 is inclined by an angle θ such that the inlet side is higher than the outlet side. Furthermore, the overflow depth at the partition plate 21 on the outlet side in the chamber 33 is taken as H. Accordingly, the weir height of the partition plate 21 on the inlet side of the chamber 33 and the weir height of the partition plate 21 on the outlet side are different from each other by H0=L sin θ. Accordingly, in order to make the weir height on the inlet side higher than the weir height on the outlet side by the overflow depth at the partition plate 21 on the outlet side, it is sufficient that H0=H, that is, L sin θ=H. Note that H can be calculated by solving the equation in description of the case in which a height difference is provided between the partition plates 21. Accordingly, θ=$\sin^{-1}$(H/L) is obtained using the calculated H together with L. If the reactor 13 is inclined by at least θ, the weir height on the inlet side is higher than the weir height on the outlet side by at least the overflow depth H at the partition plate 21 on the outlet side. If all chambers have the same length, the thus calculated θ may be used. Otherwise, it is necessary to use L that is the length of the shortest chamber. The reason for this is that the θ corresponding to the length of the shortest chamber is the largest value. Accordingly, "L" in θ=$\sin^{-1}$(H/L) may be the shortest length of the lengths, in the length direction of the reactor 13, of the respective chambers.

Figure 10:
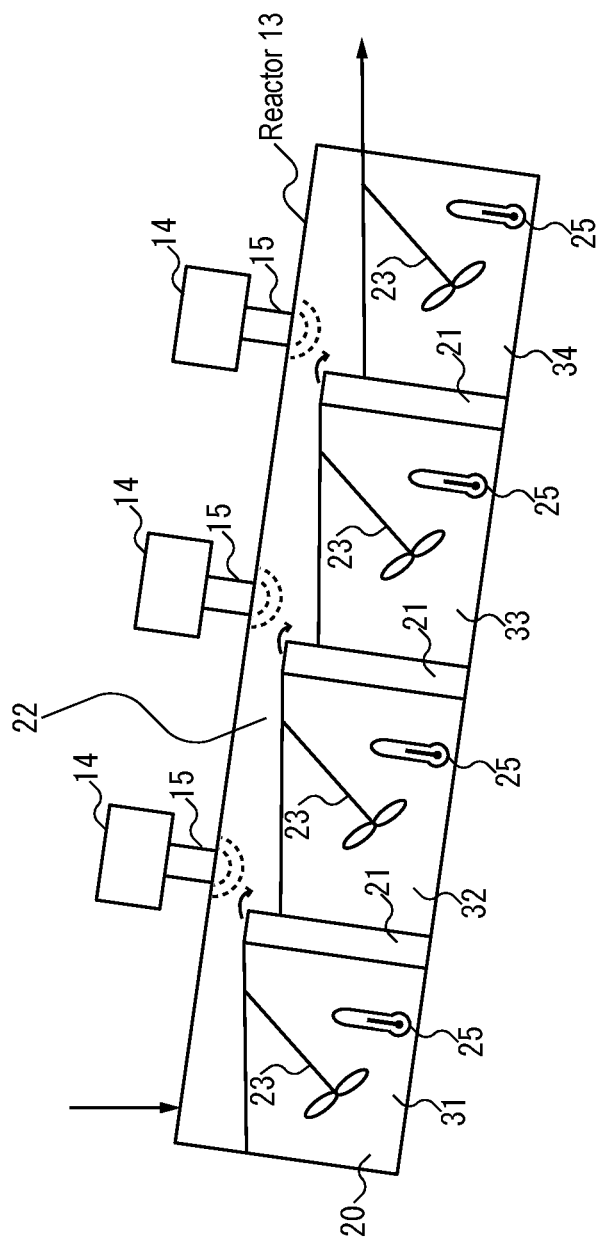
FIG. 10 is a view showing an exemplary internal configuration of the reactor that is inclined according to the embodiment.

Note that, if the reactor 13 is inclined, in the strict sense, the partition plates 21 are also inclined. Thus, the flow path at the partition plates 21 is also inclined by the angle θ. Accordingly, strictly speaking, the overflow depth is different from the value of H obtained by solving the above-described equation, but the angle θ is typically a small value, and the difference in H depending on the presence or absence of the inclination is also small. Furthermore, since H is typically sufficiently small compared with L, there is no problem even if a change in H according to the inclination of the reactor 13 is not taken into consideration. It will be appreciated that the overflow depth H may be calculated taking the inclination of the reactor 13 into consideration as well, and the thus calculated H may be used to obtain the angle θ. FIG. 10 shows an exemplary internal structure in the case where the reactor 13 is inclined.

Furthermore, also in the case where the reactor 13 is inclined, the last chamber 34 may be considered as in the case of (1). That is to say, the overflow depth at the outlet is calculated, and θ is calculated as described above, also for the last chamber 34. The reactor 13 may be inclined by at least the larger value of θ calculated for the last chamber 34 and θ calculated for the other chambers.

(3) The Case in which the Reactor is Inclined and there is a Height Difference Between the Partition Plates The above-described (1) and (2) may be combined. That is to say, in each chamber, the weir height on the inlet side can be made higher than the weir height on the outlet side by at least the overflow depth at the partition plate 21 on the outlet side, by making the reactor 13 inclined and providing a height difference between the partition plates 21. In that case, the weir height of the partition plate 21 on the inlet side may be higher than the weir height of the flow path at the partition plate 21 on the outlet side by at least "H−L sin θ". Note that H is the overflow depth at the partition plate 21 on the outlet side, L is the shortest length of the lengths, in the length direction of the reactor 13, of the respective chambers, and θ is the inclination angle of the reactor 13. Furthermore, also in this case, it is assumed that the flow paths have the same shape and are provided in the same number at the partition plates 21, and the inclination angle of the reactor 13 is not so large.

In the description of (1) to (3) above, the overflow depth H is calculated using the shape of the flow path, the flow rate, and the like, but there is no limitation to this. The overflow depth H may be measured in the state where the content is actually caused to flow inside the reactor 13. Further, the flow paths at the partition plates 21 may be designed or the inclination angle of the reactor 13 may be adjusted such that, in each chamber, the weir height on the inlet side is higher than the weir height on the outlet side by at least the overflow depth on the outlet side. In that case, the flow paths may not have the same shape and may not be provided in the same number at the partition plates 21. That is to say, the flow paths may have different shapes, may be provided in different numbers, or may have different shapes and be provided in different numbers, at the partition plates 21. Furthermore, if the overflow depth is measured, the reactor 13 may be made openable and closable above the unfilled space 22, or may be provided with a window through which the inside of the reactor 13 can be observed from above the unfilled space 22. In the latter case, the window preferably does not transmit microwaves, but, if the window transmits microwaves, the window may be covered by a material that does not transmit microwaves during irradiation of microwaves, and, only at the time of observation, the irradiation of microwaves may be stopped and the cover may be opened to perform the observation. In this case, the reactor 13 being openable and closable refers to the configuration in which the reactor 13 is provided with a lid member that can be opened and closed. The lid member may be, for example, an upper face plate of the reactor 13, may be a door-like member, or may be another openable and closable member. Furthermore, if the overflow depth is measured, for example, scales for measuring the overflow depth may be provided at the flow paths at the positions of the partition plates 21.

In the case of the first chamber 31 of the reactor 13, that is, the chamber into which the content is loaded from the outside, the content is typically loaded from above as shown in FIG. 2 and the like. Thus, consideration of the conditions relating to the partition plates 21 and the inclination angle as in the case of (1) to (3) described above is not necessary. However, if the content is caused to flow horizontally into the first chamber 31 as in the case of the following chambers, also in the first chamber 31, the weir height on the inlet side (the height of the bottom of the flow path) may be set higher than the weir height on the outlet side by at least the overflow depth at the partition plate 21 on the outlet side, as described above.

Figure 4C:
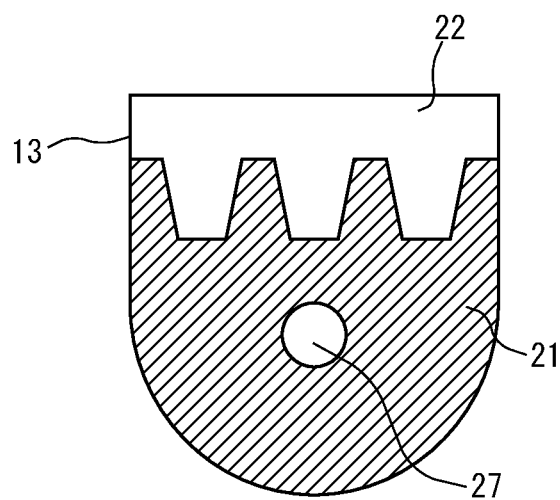
FIG. 4C is a view showing an exemplary shape of the partition plate according to the embodiment.
Figure 4D:
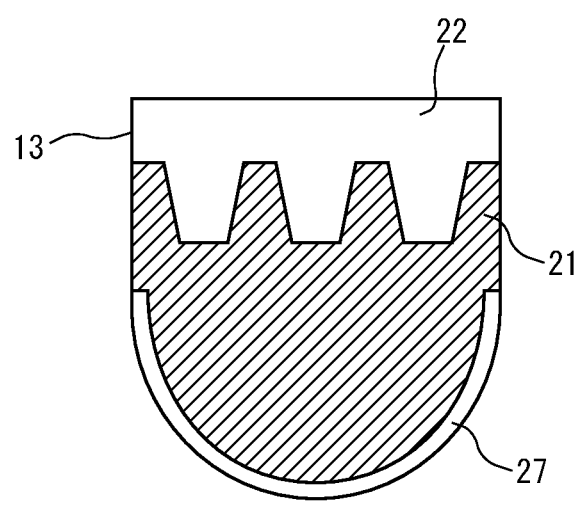
FIG. 4D is a view showing an exemplary shape of the partition plate according to the embodiment.

Furthermore, the flow path at the partition plates 21 may or may not include a flow path that allows the content to flow through a void of the partition plates 21 in addition to the flow path that allows the content to flow over the partition plates 21. That is to say, "the content flows over each of the partition plates 21" refers to that at least the overflow-type flow path is present, and does not refer to that another flow path should not be present. In the former case, that is, if there is a flow path that allows the content to flow through a void of the partition plates 21, the void may be a void 27 provided through the partition plate 21 as shown in FIG. 4C, may be a void 27 between the partition plate 21 and the reactor 13 as shown in FIG. 4D, or may be both voids. There is no limitation on the shape, the position, and the number of voids 27. Furthermore, if the partition plate 21 has the void 27, it is preferable that the content through the void 27 does not flow in a shortcut. Accordingly, for example, adjacent partition plates 21 may be arranged such that the partition plate 21 shown in FIG. 4C and the partition plate 21 shown in FIG. 4D are alternately arranged. Furthermore, if the partition plate 21 has the void 27, the overflow depth H may be calculated taking the flow rate through that void into consideration as well, or the overflow depth H may be measured as described above. Furthermore, if the partition plate 21 has the void 27, the flow path through the void 27 may allow part of the content to flow from the downstream side to the upstream side.

In the case where the reactor 13 is not inclined, the object can be realized also by making, in each chamber, the weir height on the inlet side higher than the weir height on the outlet side by at least five times or ten times the overflow depth at the partition plate 21 on the outlet side. However, with this configuration, a difference between the liquid surfaces of the respective chambers increases, and the capacity of the chamber decreases toward the downstream side, so that the amount of material that can be treated by the reactor 13 decreases. Accordingly, it is preferable that the difference between the weir height on the inlet side and the weir height on the outlet side in each chamber is not extremely large, although the difference has to be at least the overflow depth at the partition plate 21 on the outlet side. The difference between the weir heights may be, for example, approximately one to three times the overflow depth on the outlet side. Furthermore, also in the case where the reactor 13 is inclined, the capacity of each chamber decreases as the inclination angle is increased. Accordingly, it is preferable that the inclination angle is set such that the difference between the weir height on the inlet side and the weir height on the outlet side in each chamber is not extremely large, although the difference has to be at least the overflow depth at the partition plate 21 on the outlet side. Also in this case, the inclination angle may be set such that the difference between the weir heights is, for example, approximately one to three times the overflow depth on the outlet side. Note that, since the content flows into or flows out of each chamber, the height of the liquid surface may slightly increase or decrease in each chamber. Accordingly, as a precautionary measure, the partition plates 21 may be designed or the reactor 13 may be inclined such that, in each chamber, the difference between the weir height on the inlet side and the weir height on the outlet side is approximately two to three times the overflow depth on the outlet side. Furthermore, if agitation is performed using the agitation units 23, the partition plates 21 may be designed or the reactor 13 may be inclined, using the overflow depth H when no agitation is performed.

Hereinafter, a specific example for computing the overflow depth and the like will be described. If flow rate $Q=1000$ (liter/hour)$=2.78 \times 10^{-4}$ (m$^3$/s), width a of bottom of flow path$=0.01$ (m), width b of upper side of flow path$=0.1$ (m), height e of flow path$=0.05$ (m), flow coefficient $C=0.6$, number N of flow paths$=3$, and acceleration of gravity $g=9.807$ (m/s$^2$), $$H=0.017 \text{ (m)}.$$

In the equation, H is obtained by numerical computation. Accordingly, in the case of (1) above, it is sufficient that, in each chamber, the weir height of the partition plate 21 on the upstream side is higher than the weir height of the partition plate 21 on the downstream side by at least 1.7 cm. Accordingly, for example, the partition plates 21 may be designed such that the weir height of the partition plates 21 in the reactor 13 decreases stepwise by 2 cm toward the downstream side. Furthermore, in the case of (2) above, if the length L of each chamber$=0.5$ (m), then $\theta=0.035$ (rad)$=2.0°$. Accordingly, it is sufficient that the reactor 13 is inclined by 2°.

Next, an operation of the chemical reaction apparatus 1 according to this embodiment will be briefly described. The raw material and the catalyst are supplied by the pumps 11 to the mixing portion 12, are mixed in the mixing portion 12, and are loaded into the reactor 13. The speed of the raw material and the like supplied to the reactor 13 may be preferably in accordance with the flow rate Q.

The raw material and the like supplied to the reactor 13 flow from the upstream side to the downstream side while being agitated by the agitation units 23. The microwaves generated by the microwave generators 14 are transmitted via the waveguides 15 to the unfilled space 22 in the reactor 13, and are irradiated on the raw material and the like. At that time, overflows are not directly connected as described above, and, thus, the content can be prevented from flowing in a shortcut, and the content can be efficiently irradiated with microwaves. The raw material and the like are heated with the microwaves, and the reaction of the raw material and the like is facilitated. Note that the temperatures of the chambers 31 to 34 are measured by the temperature measuring portions 25, and are passed to the microwave control portion 16 via a route that is not shown. Then, the microwave control portion 16 controls the power of the microwave generators 14 such that the temperatures of the chambers 31 to 34 are at a desired temperature or in a desired temperature range.

The product material discharged from the reactor 13 is loaded into the catalyst separating portion 17 where the catalyst is separated therefrom. Then, the product material from which the catalyst has been separated is loaded by the pump 11 into the treated liquid storage tank 18. In the treated liquid storage tank 18, the product material is separated into a target product and a by-product. In this manner, a final product is obtained. Furthermore, such treatment is repeatedly performed, and, thus, a target product is sequentially produced.

Note that the treatment that separates the catalyst in the catalyst separating portion 17 and the treatment that separates the product material into a product and a by-product in the treated liquid storage tank 18 may be performed sequentially each time the product material is loaded, or may be performed at a time when the amount of product material loaded accumulates and reaches a certain amount. That is to say, the treatment in the reactor 13 is of a flow-type (flow through-type), but the treatment in the catalyst separating portion 17 and the treated liquid storage tank 18 on the path thereafter may be of a flow-type, or may be of a batch-type.

Furthermore, there is no limitation on the chemical reaction caused to occur in the chemical reaction apparatus 1 according to this embodiment, as long as it is a chemical reaction that is caused to occur by microwave irradiation itself or by heat due to microwave irradiation. For example, the chemical reaction may be production of biodiesel fuel through esterification or transesterification, may be production of ink raw material that is ester, or may be other chemical reactions.

Next, a case will be described in which biodiesel fuel (fatty acid methyl ester) is produced from waste oil using the chemical reaction apparatus 1 according to this embodiment. It will be appreciated that the present invention is not limited to this reaction.

Reaction System Construction Example

As the raw material, a mixture of fat and oils and free fatty acid, and alcohol are used. The alcohol is used as a reactant. The raw material and the catalyst are sent by the pumps 11 into the mixing portion 12, and are uniformly mixed. The mixed liquid is supplied to the reactor 13. The mixed liquid inside the reactor 13 is irradiated with the microwaves generated by the microwave generators 14, and, thus, the esterification reaction is facilitated. Furthermore, the mixed liquid inside the reactor 13 is loaded into the chambers 31 to 34 that have been partitioned from each other by the partition plates 21 inside the reactor 13. The mixed liquid together with the catalyst is irradiated with microwaves while being agitated by the agitation units 23, and, thus, the reaction progresses. The microwaves are irradiated on the unfilled space 22 inside the reactor 13, and are diffused inside the reactor 13. The reaction liquid in each chamber moves to its next chamber through a flow path provided at the partition plates 21. The reaction liquid is held inside the reactor 13 for a certain retention time, and then is discharged out of the reactor 13. The mixed liquid after the reaction discharged out of the reactor 13 is supplied to the catalyst separating portion 17. After the catalyst is separated in the catalyst separating portion 17, the mixed liquid is loaded into the treated liquid storage tank 18. From the reaction liquid after the catalyst separation, water and glycerin that are by-products are further separated in the treated liquid storage tank 18, and, thus, crude methyl ester that is a target product is obtained. The microwave power of the reactor 13 is subjected to feedback control based on the temperatures inside the chambers 31 to 34, and, thus, the temperatures of the chambers 31 to 34 are kept constant. For example, the reaction temperature may be set at 70° C.

As described above, with the chemical reaction apparatus 1 according to this embodiment, overflows can be prevented from being directly connected in the horizontal direction between the chambers, by changing the height of the flow path at the partition plates 21, making the reactor 13 inclined, or applying both of these configurations. Accordingly, the content can be prevented from flowing in a shortcut, so that the content can be irradiated with microwaves as appropriate. As a result, an unreacted content is prevented from being discharged out of the reactor 13, and the yield in the chemical reaction apparatus 1 can be improved. Since the content inside the reactor 13 is agitated using the agitation units 23, the content can be uniformly irradiated with microwaves even in the case where the depth to which microwaves penetrate is not so deep. Furthermore, since the reactor 13 is partitioned into multiple chambers, the content undergoes a reaction while being retained in each chamber, and, thus, the content can be effectively irradiated with microwaves in each chamber. Furthermore, if the solid catalyst is microwave-absorbing or microwave-sensitive, the solid catalyst is efficiently heated through microwave irradiation, and, thus, the chemical reaction near the solid catalyst can be facilitated. In this manner, the chemical reaction inside the reactor 13 is facilitated, and, thus, a product material can be more efficiently obtained.

Note that, in this embodiment, the case has been mainly described where the reactor 13 in which the area of the liquid surface does not change according to a change in the amount of the content is shaped such that the side face of the reactor 13 extends in the normal direction of the liquid surface as shown in FIGS. 3A and 3B, but there is no limitation to this. The reactor 13 may have a shape in which the area of the liquid surface does not change according to a change in the amount of the content also in the case where the side face of the reactor 13 extends in a direction different from the normal direction of the liquid surface. This configuration is realized, for example, in the case where the reactor 13 is installed so as to be inclined as shown in FIG. 10.

Figure 3C:
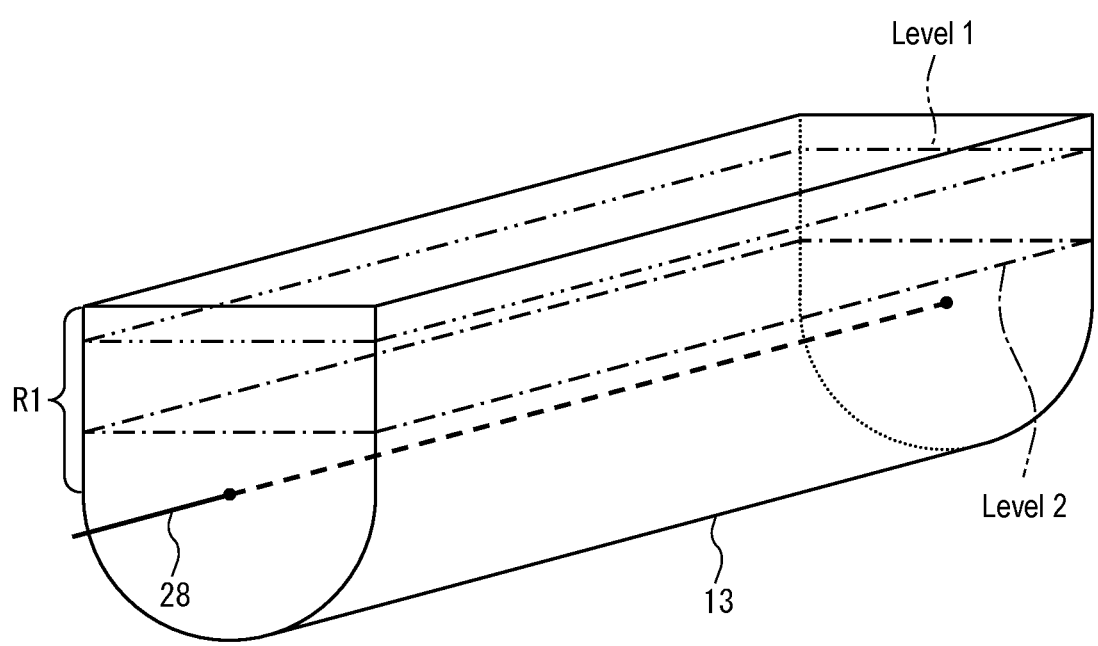
FIG. 3C is a perspective view showing an exemplary shape of the reactor according to the embodiment.
Figure 3D:
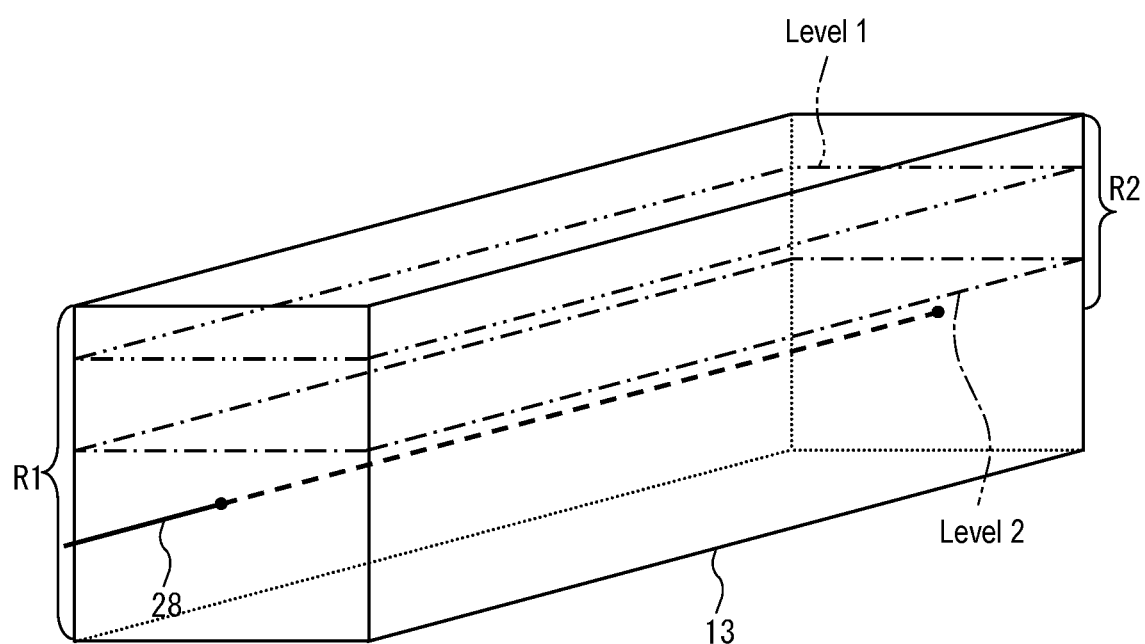
FIG. 3D is a perspective view showing an exemplary shape of the reactor according to the embodiment.

Furthermore, the case has been described with reference to FIG. 2 where each chamber has the agitation unit 23, but there is no limitation to this. Multiple chambers may have a single or multiple agitation units 23. If the chemical reaction apparatus 1 has a single agitation unit 23, as described above, the agitation unit 23 may have a shaft (rotational shaft) shared by multiple chambers. In that case, the agitation unit 23 may include a rotational shaft, multiple rotatable members, and a rotating unit. The rotational shaft is a shaft extending in the flow direction in the reactor 13. For example, in FIG. 2, the rotational shaft may extend from the left end face to the right end face of the reactor 13. The rotational shaft may be provided in parallel to the bottom face of the reactor 13. For example, this rotational shaft may be made of a microwave-transmitting material, a microwave-absorbing material, a microwave-reflecting material, or a combination of two or more freely selected from these materials. If the rotational shaft is made of a microwave-reflecting material (e.g., metal, etc.), microwaves irradiated on the rotational shaft are reflected. Accordingly, if the rotational shaft is present above the liquid surface of the content inside the reactor 13 in this case, part of the microwaves is reflected by the rotational shaft and is not irradiated on the content. Accordingly, in order to avoid such a situation, it is preferable that the liquid surface of the content is positioned above the rotational shaft, that is, the rotational shaft is present inside the content. Furthermore, if the rotational shaft is made of a microwave-absorbing material, microwaves irradiated on the rotational shaft are absorbed. Accordingly, if the rotational shaft is present above the liquid surface of the content inside the reactor 13 in this case, part of the microwaves is absorbed by the rotational shaft and is not irradiated on the content. Furthermore, the heat of the rotational shaft may abnormally increase. Accordingly, in order to avoid such a situation, it is preferable that the liquid surface of the content is positioned above the rotational shaft, that is, the rotational shaft is present inside the content. Accordingly, the amount of the content may be controlled such that the liquid surface of the content is above the rotational shaft, or the reactor 13 may have a shape in which the cross-sectional area in the liquid surface direction does not change at least above the rotational shaft. For example, as shown in FIG. 3C, the height of the liquid surface at the lowest level in the range R1 in which the area of the liquid surface does not change may be set to the height at which the content just covers a rotational shaft 28. Accordingly, if the liquid surface is within the range R1, the area of the liquid surface does not change, and the liquid surface is positioned above the rotational shaft 28. Note that, in FIG. 3C, the radius of the semicylindrical shape forming the lower portion of the reactor 13 is preferably in accordance with the rotational radius of the rotatable members rotating about the rotational shaft 28. This configuration can effectively prevent a situation in which part of the content at the bottom of the reactor 13 fails to be agitated. Furthermore, for example, in the case of the reactor 13 shown in FIG. 3D in which the area of the liquid surface does not change as long as the height of the liquid surface of the content is within the range R1, which covers the entire height, the control can be performed such that the area of the liquid surface does not change, and such that the liquid surface is positioned above the rotational shaft 28, by keeping the height of the liquid surface within the range R2. The height of the liquid surface at the lowest level in the range R2 is set to the height at which the content just covers the rotational shaft 28. Note that "above" and "below" are directions along the vertical direction. The same is applicable to "upper side" and "lower side". Furthermore, "vertical direction" is a direction perpendicular to the horizontal plane. The flow direction in the reactor 13 is the flow direction of the content in the reactor 13, and is typically the same as the length direction of the reactor 13. The rotatable members are members that rotate about the rotational shaft. When the rotatable members rotate, the content is rotationally agitated. The rotatable members may be, for example, blade-like members, wing-like members, rod-like members, or the like, as described above. Furthermore, each chamber may have such a rotatable member, but there is no limitation to this. There may be a chamber having no rotatable member. Furthermore, one chamber may have two or more rotatable members. It is sufficient that the agitation units 23 have at least one or more rotatable members. The rotating unit rotates each rotatable member. If the rotatable members are fixed to the rotational shaft, the rotating unit may be a unit for rotating that rotational shaft. In that case, the rotating unit may be, for example, a motor, an engine, or the like. Furthermore, the rotational shaft may not rotate, but may support the rotatable member in a rotatable manner. In that case, for example, the rotating unit may rotate a rotatable member having a magnet, using a magnetic force. Specifically, as in the case of a motor that rotates a rotor configured by a permanent magnet, using a stator configured by an electromagnet provided around the rotor, it is possible to rotate the rotatable member (rotor) using the rotating unit (stator). Note that, in that case, the rotating unit that is a stator is preferably disposed outside the reactor 13, but there is no limitation to this. The reason for this is that, depending on the material forming the reactor 13, the rotating unit that is a stator cannot be disposed outside the reactor 13. Furthermore, if the agitation units 23 have a rotational shaft extending in multiple chambers, holes through which the rotational shaft extends may be formed in the partition plates 21. Furthermore, if there is a rotational shaft extending in multiple chambers, the rotational shaft may extend through the voids 27 of the partition plates 21.

Furthermore, in this embodiment, the case has been described where the reactor 13 has a shape in which the cross-section in the liquid surface direction of the content does not change as long as the amount of the content is within a predetermined range, but there is no limitation to this. If the reactor 13 has a shape that ultimately prevents the area of the liquid surface from changing according to a change in the amount of the content as long as the amount of the content is within a predetermined range, it is not necessary that the cross-section in the liquid surface direction of the content does not change. Specifically, even in the case where the cross-section in the liquid surface direction of the content changes from one shape (e.g., rectangle, etc.) to another shape (e.g., trapezoid, etc.) according to the height of the liquid surface, as long as the cross-sectional area in the liquid surface direction of the content is the same throughout the height of the liquid surface, it can be said that the reactor 13 has a shape in which the area of the liquid surface does not change according to a change in the amount of the content even in the case where the cross-section in the liquid surface direction of the content changes.

Furthermore, in this embodiment, the case has been described where the reactor 13 has a shape in which the area of the liquid surface does not change even in the case where the height of the liquid surface changes according to a change in the amount of the content as long as the amount of the content is within a predetermined range, but there is no limitation to this. The area of the liquid surface may change according to a change in the amount of the content.

Furthermore, in this embodiment, there is no limitation on the number of rotational shafts or rotating units in the agitation units 23. For example, a single rotational shaft and a single rotating unit may be used to rotate one or more rotatable members, or two or more rotational shafts and two or more rotating units may be used to rotate two or more rotatable members.

In this embodiment, the case has been described where the mixing portion 12 that mixes the raw material and the catalyst is provided, but there is no limitation to this. For example, if a premixture of the raw material and the catalyst is used, if the mixing is also performed by the reactor 13, if the solid catalyst that flows inside the reactor 13 is retained in the reactor 13, or if a solid catalyst forming a fixed bed is used instead of the solid catalyst that flows inside the reactor 13, the chemical reaction apparatus 1 does not have to be provided with the mixing portion 12. Note that, if a solid catalyst forming a fixed bed is used, typically, the solid catalyst forming a fixed bed is provided inside the reactor 13. The solid catalyst forming a fixed bed may be fixed, for example, by being pasted on the inner wall of the reactor 13, or by being placed in a catalyst filled layer, a column, or the like inside the reactor 13. Examples of the shape of the solid catalyst include various grains, a cylinder (that may or may not be hollow), a sphere, a pellet, a ring, a shell, a honeycomb, a foam, a fiber, a cloth, a plate, and other shapes.

Furthermore, in this embodiment, the case has been described where the reactor 13 has four chambers 31 to 34 that are continuously arranged in series as shown in FIG. 2, but there is no limitation on the number of chambers. Typically, as the number of chambers increases, a situation can be more effectively prevented in which the raw material flows in a shortcut from the inlet to the outlet of the reactor 13. Furthermore, if the capacity of each chamber does not change regardless of an increase or a decrease in the number of chambers, the retention time from when the content of the reactor 13 flows into the reactor 13 to when the content flows out of the reactor 13 becomes longer as the number of chambers increases, and the retention time becomes shorter as the number of chambers decreases. Accordingly, in this case, the number of chambers can be adjusted such that a desired retention time is obtained.

Figure 11:
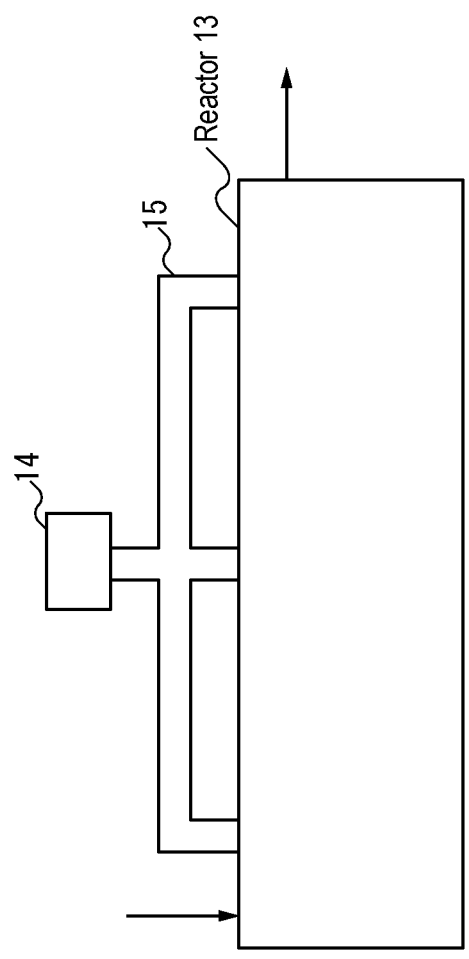
FIG. 11 is a view showing another exemplary microwave generator and waveguide according to the embodiment.

Furthermore, in this embodiment, the case has been described where the multiple microwave generators 14 are provided, but there is no limitation to this. For example, the microwaves generated by the microwave generator 14 may be transmitted via a branched waveguide 15 to multiple locations as shown in FIG. 11. The multiple locations may be, for example, multiple chambers. FIG. 11 shows the case in which the chemical reaction apparatus 1 is provided with only one microwave generator 14, but, in the case where the chemical reaction apparatus 1 is provided with two or more microwave generators 14, the microwaves generated by any one of the multiple microwave generators 14 may be transmitted via the branched waveguide 15 to multiple locations. For example, if the microwaves generated by the microwave generator 14 are transmitted to multiple chambers, the microwave control portion 16 may control the power of that microwave generator 14 using any or all of the temperatures of the chambers to which the microwaves generated by the microwave generator 14 are transmitted. For example, the microwave control portion 16 may perform the control using an average of all temperatures of the chambers, or may perform the control using a maximum value or a minimum value of the temperatures of the chambers.

Furthermore, in this embodiment, the case has been described where the chemical reaction apparatus 1 is provided with the temperature measuring portions 25 and the microwave control portion 16, but there is no limitation to this. For example, if it is possible to keep the temperature inside the reactor 13 at a desired temperature or in a desired temperature range by setting the power of microwaves to a predetermined value, the control of the power of microwaves using the temperature does not have to be performed.

Furthermore, in this embodiment, the case has been described where the catalyst separating portion 17 is provided on the path after the reactor 13, but there is no limitation to this. If the catalyst does not have to be separated by the chemical reaction apparatus 1 according to this embodiment, as in the case in which the catalyst is separated by another apparatus, the case in which the solid catalyst that flows inside the reactor 13 is retained in the reactor 13, the case in which a solid catalyst forming a fixed bed is used instead of the solid catalyst that flows inside the reactor 13, or the case in which no catalyst is used in the chemical reaction in the reactor 13, the catalyst separating portion 17 does not have to be provided.

Furthermore, in this embodiment, the case has been described where the raw material and the catalyst are mixed and loaded into the reactor 13, but there is no limitation to this. For example, only the raw material may be loaded into the reactor 13. Furthermore, if the raw material and the catalyst are not mixed, only the raw material may flow inside the reactor 13. That is to say, the content of the reactor 13 may be, for example, a mixture of multiple raw materials. Furthermore, even in the case where the raw material and the catalyst are not mixed, for example, the raw material and the catalyst may flow inside the reactor 13 when the solid catalyst that flows inside the reactor 13 is retained in the reactor 13. Furthermore, if the raw material and the catalyst are not mixed, the mixing portion 12 may, for example, mix the raw material, or mix the raw material (substrate) and the reactant. Furthermore, if the raw material and the like do not have to be mixed, the chemical reaction apparatus 1 does not have to be provided with the mixing portion 12 as described above.

Furthermore, in this embodiment, the case has been described where one or more agitation units 23 that agitate the raw material inside the reactor 13 are provided, but there is no limitation to this. For example, if the reactor 13 is configured such that the entire raw material can be easily irradiated with microwaves (e.g., if the inner diameter of the reactor 13 is small, etc.), the agitation units 23 do not have to be provided.

Furthermore, in this embodiment, the case has been described where the chemical reaction apparatus 1 is provided with the treated liquid storage tank 18, but there is no limitation to this. For example, a mixture of the product material and the by-product discharged from the chemical reaction apparatus 1 may be subjected to extraction of the product material and the like in another apparatus.

Figure 12A:
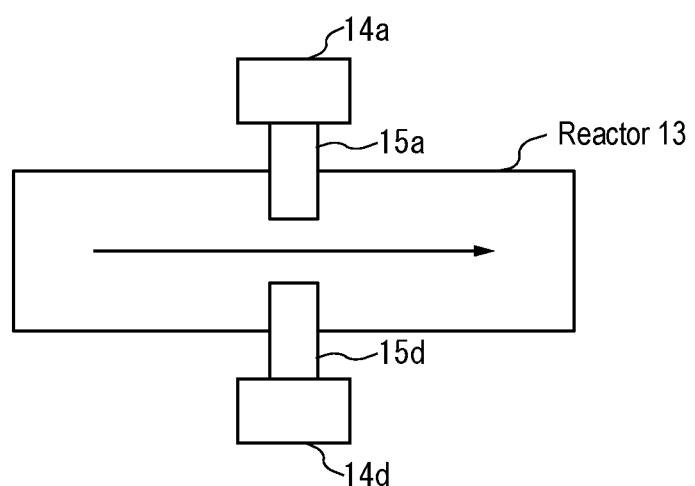
FIG. 12A is a view illustrating a position for microwave irradiation according to the embodiment.
Figure 12B:
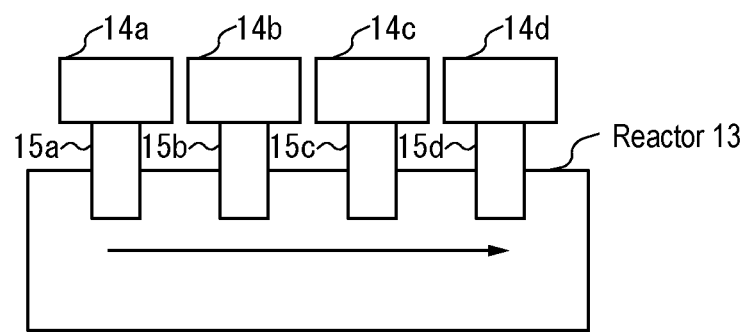
FIG. 12B is a view illustrating positions for microwave irradiation according to the embodiment.

Furthermore, in this embodiment, the chemical reaction apparatus 1 may be provided with two or more microwave generators 14, and the two or more microwave generators 14 may generate microwaves having two or more frequencies. That is to say, the content of the reactor 13 may be irradiated with microwaves having two or more frequencies. In that case, the microwaves having two or more frequencies may be irradiated on the same position, or may be respectively irradiated on different positions. For example, as shown in FIG. 12A, microwaves having frequencies X and Y respectively generated by microwave generators 14a and 14d may be irradiated on the same position in the reactor 13, that is, at the midstream in the reactor 13. Note that the microwaves having the frequencies X and Y are respectively transmitted via waveguides 15a and 15d to the reactor 13. Furthermore, for example, as shown in FIG. 12B, microwaves having a frequency X generated by microwave generators 14a, 14b, and 14c may be irradiated on the side from the upstream to the midstream in the reactor 13, and microwaves having a frequency Y generated by a microwave generator 14d may be irradiated on the downstream side in the reactor 13. Note that the microwaves having the frequency X are respectively transmitted via waveguides 15a, 15b, and 15c to the reactor 13. Furthermore, the microwaves having the frequency Y are transmitted via a waveguide 15d to the reactor 13. FIGS. 12A and 12B are both views of the reactor 13 from above, wherein the arrows in the drawings indicate the flow of the content inside the reactor 13. If microwaves having two or more frequencies are irradiated, the number of frequencies may be two, or three or more. There is no limitation on the combination of two or more frequencies, as long as they are selected from the range from 300 MHz to 300 GHz. For example, if microwaves having two frequencies are irradiated, examples of the combination of these frequencies include 2.45 GHz and 5.8 GHz, 2.45 GHz and 24 GHz, 2.45 GHz and 913 MHz, 5.8 GHz and 24 GHz, 5.8 GHz and 913 MHz, and 24 GHz and 913 MHz. Furthermore, if microwaves having two or more frequencies are irradiated, there is no limitation on the irradiation timing. For example, microwaves having two or more frequencies may be simultaneously irradiated, or may be irradiated respectively in different irradiation periods. For example, in the latter case, microwaves having the frequency X may be irradiated in one period, and microwaves having the frequency Y may be irradiated in the next period. Furthermore, if microwaves having two or more frequencies are irradiated, the microwaves having two or more frequencies may be introduced to one unfilled space 22, or may be introduced to different unfilled spaces 22. In the latter case, there are at least two or more unfilled spaces 22 that have been separated from each other by the partition plate 21 inside the reactor 13. Note that if microwaves having two or more frequencies are irradiated, a material that is not affected by the action (e.g., heating, etc.) of microwaves having one frequency can be also affected, and, thus, a wider range of materials can be affected by the microwaves.

Figure 13:
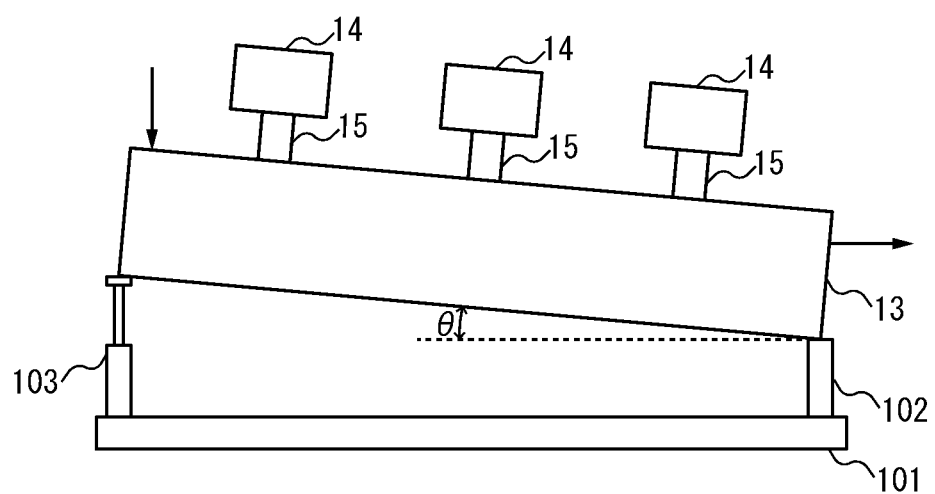
FIG. 13 is a view illustrating an inclination angle changing mechanism of the reactor according to the embodiment.

Furthermore, in this embodiment, the chemical reaction apparatus 1 may also further include an inclination angle changing mechanism for changing the inclination angle of the reactor 13. It is assumed that, in the reactor 13, as described above, one or more weirs that are flow paths of the content 20 are formed in the upper portion of each of the partition plates 21. If the reactor 13 is not inclined, the partition plates 21 may have the same weir height. That is to say, it is also possible that the lower portions of the multiple partition plates 21 extend to the bottom face of the reactor 13, and the lengths from the lower portions to the weirs of the partition plates 21 (the lengths from the lower portions to the bottoms of the flow paths of the partition plates 21) are the same. That is to say, the situation may be similar to that of (2) above. Hereinafter, an example of the inclination angle changing mechanism will be described with reference to FIGS. 13 and 14. FIG. 13 is a view showing a case in which the inclination angle changing mechanism has a jack 103, and FIG. 14 is a view showing a case in which the inclination angle changing mechanism has a winch 202.

Referring to FIG. 13, the chemical reaction apparatus 1 includes a base 101 that is arranged in the horizontal direction, a support portion 102 that supports the bottom on the downstream side of the reactor 13, on the base 101, and a jack 103 that supports the bottom on the upstream side of the reactor 13, on the base 101. The jack 103 can change the height of the bottom on the upstream side of the reactor 13. Accordingly, the jack 103 can change the inclination angle θ of the reactor 13. The jack 103 may be, for example, a mechanical jack, a hydraulic jack, or the like. It is preferable that, when the upstream side (the left side in FIG. 13) in the reactor 13 is vertically moved by the jack 103, the position of the bottom at the downstream end of the reactor 13 (the lower right end of the reactor 13 in FIG. 13) does not change. Accordingly, the support portion 102 may support the bottom on the downstream side of the reactor 13 by means of a hinge or the like. Furthermore, the inclination angle of the reactor 13 may also be changed by changing, using the jack 103, the height of the bottom on the downstream side of the reactor 13 in a state in which the height of the bottom on the upstream side of the reactor 13 is fixed.

Figure 14:
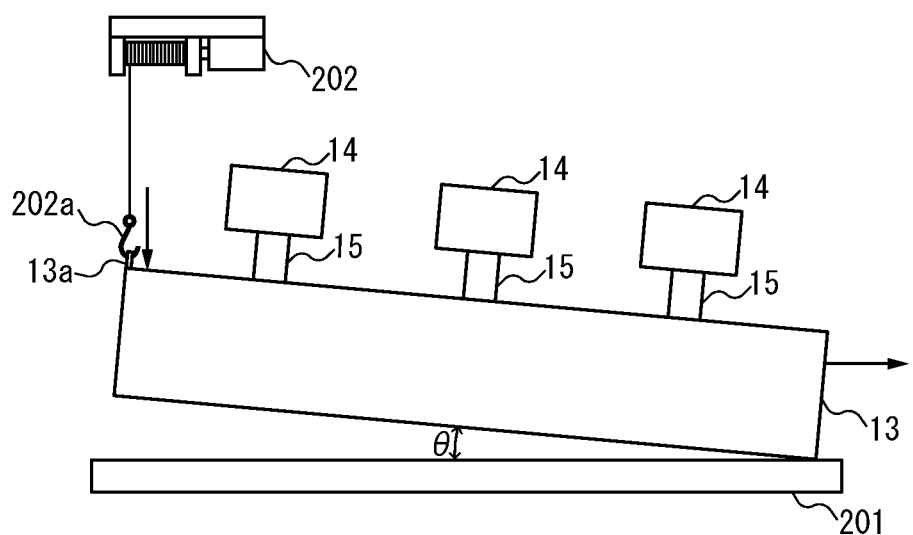
FIG. 14 is a view illustrating an inclination angle changing mechanism of the reactor according to the embodiment.

Referring to FIG. 14, the chemical reaction apparatus 1 includes a base 201 that is arranged in the horizontal direction, and a winch 202 that vertically moves the upstream side of the reactor 13. The upper face on the upstream side of the reactor 13 is provided with a ring-shaped member 13a. The height on the upstream side of the reactor 13 can be changed by winding up or letting out a wire rope using the winch 202 in a state in which a hook 202a at an end of a wire rope extending from the winch 202 is caught on the ring-shaped member 13a. As a result, the inclination angle θ of the reactor 13 can be changed. Note that the bottom on the downstream side of the reactor 13 is supported by the base 201. It is preferable that, when the upstream side of the reactor 13 is vertically moved by the winch 202, the position of the bottom at the downstream end of the reactor 13 does not change. Accordingly, the base 201 may support the bottom on the downstream side of the reactor 13 by means of a hinge or the like. Furthermore, the height on the upstream side of the reactor 13 may also be changed by a unit other than the winch 202. For example, the height on the upstream side of the reactor 13 may be changed using a manual or electric chain block.

The inclination angle of the reactor 13 may be changed, for example, within a range in which, in each of the chambers 31 to 34, the weir height on the inlet side is higher than the weir height on the outlet side by at least the overflow depth at the partition plate on the outlet side, when the content 20 flows inside the reactor 13. For example, the inclination angle θ of the reactor 13 may be changed within a range in which it is $\sin^{-1}(H/L)$ or more. The inclination angle θ is changed by the above-described inclination angle changing mechanism.

The inclination angle of the reactor 13 may be changed, for example, according to the state of the content 20. The state of the content 20 may be, for example, the temperature of the content 20, the viscosity of the content 20, the temperature and the viscosity of the content 20, or another state of the content 20. The temperature of the content 20 may be measured, for example, by the temperature measuring portions 25. The viscosity of the content 20 may be measured, for example, by a viscosity sensor. The viscosity sensor may be, for example, an ultrasonic viscometer that measures viscosity using ultrasonic waves, or may be a rotational viscosimeter that measures viscosity using viscous resistance of a rotor. For example, a configuration may also be employed where, until the state of the content 20 satisfies a predetermined condition, the inclination angle of the reactor 13 is set to θ1, and, when the state of the content 20 satisfies the predetermined condition, the inclination angle of the reactor 13 is changed from θ1 to θ2. Specifically, when the viscosity of the content 20 becomes greater than a threshold value, the inclination angle of the reactor 13 may be changed from θ1 to θ2. In this case, θ2>θ1. For example, if the viscosity of the content 20 is low at the start of a chemical reaction inside the reactor 13 but increases as the chemical reaction progresses, a preferable inclination angle according to the state of the chemical reaction can be obtained by changing the inclination angle in accordance with the viscosity as described above. If the viscosity decreases in accordance with an increase in the temperature of the content 20, the inclination angle of the reactor 13 may be decreased from θ1 to θ2 when the temperature of the content 20 becomes greater than a threshold value. In this case, θ1>θ2. In this manner, the inclination angle can be dynamically adjusted such that the content 20 properly flows inside the reactor 13.

The inclination angle of the reactor 13 may be changed, for example, according to the type of content 20. For example, if the material that is loaded into the reactor 13 is switched from a first material to a second material, the content 20 is gradually replaced from the first material to the second material. In this case, the inclination angle of the reactor 13 may be changed from an inclination angle θ1 that is preferable for the first material, to an inclination angle θ2 that is preferable for the second material. For example, if the viscosity of the second material is greater than the viscosity of the first material, the inclination angle of the reactor 13 may be increased from θ1 to θ2 when the content 20 is replaced from the first material to the second material. In this manner, the inclination angle can be dynamically adjusted such that the content 20 properly flows inside the reactor 13.

The inclination angle of the reactor 13 may be changed, for example, according to the amount of content 20 that is loaded into the reactor 13 per unit time. For example, if the amount of content 20 that is loaded into the reactor 13 per unit time increases, the flow rate Q of the content 20 increases in accordance with the increase, and the overflow depth H increases. Thus, the inclination angle of the reactor 13 may be increased in accordance with an increase in the overflow depth H. On the other hand, for example, if the amount of content 20 that is loaded into the reactor 13 per unit time decreases, the flow rate Q of the content 20 decreases in accordance with the decrease, and the overflow depth H decreases. Thus, the inclination angle of the reactor 13 may be decreased in accordance with a decrease in the overflow depth H. In this manner, the inclination angle can be dynamically adjusted such that the content 20 does not flow in a shortcut inside the reactor 13.

The inclination angle of the reactor 13 may be changed, for example, by a control unit for controlling the inclination angle changing mechanism, or by an operator manually operating the inclination angle changing mechanism. In the case of the former, the control unit may control the inclination angle of the reactor 13, for example, according to measured values of sensors for acquiring states of the content 20, or the type or the loaded amount of the content 20 input by a worker or the like.

Furthermore, in the foregoing embodiment, information relating to the processing performed by each constituent element, for example, information that is to be accepted, acquired, selected, produced, transmitted, or received by each constituent element, information such as a threshold value, a numerical expression, or an address used in each constituent element in the processing and the like may be retained in an unshown storage medium temporarily or for a long period of time even if not specified in the description above. Furthermore, information may be accumulated in the unshown storage medium by each constituent element or by an unshown accumulating unit. Furthermore, information may be read from the unshown storage medium by each constituent element or by an unshown reading unit.

Furthermore, in the foregoing embodiment, if information used in each constituent element or the like, for example, information such as a threshold value, an address, or various setting values used in each constituent element in the processing may be changed by a user, the user may change such information as appropriate even if not specified in the description above, but there is no limitation to this. If the user may change such information, the change may be realized by, for example, an unshown accepting unit that accepts a change instruction from the user and an unshown changing unit that changes information according to the change instruction. The change instruction may be accepted by the unshown accepting unit, for example, by accepting information from an input device, by receiving information transmitted via a communication line, or by accepting information read from a predetermined storage medium.

Furthermore, in the foregoing embodiment, each constituent element may be configured by dedicated hardware, or, alternatively, constituent elements that can be realized by software may be realized by executing a program. For example, each constituent element may be realized by a program execution unit such as a CPU reading and executing a software program stored in a storage medium such as a hard disk or a semiconductor memory.

Furthermore, it will be appreciated that the present invention is not limited to the embodiment set forth herein, and various modifications are possible within the scope of the present invention.

As described above, the chemical reaction method using the chemical reaction apparatus according to the present invention is effective in that a content can be prevented from flowing in a shortcut, and, thus, it is useful, for example, as a chemical reaction method using a chemical reaction apparatus for performing microwave irradiation.

The invention claimed is:

1. A chemical reaction method comprising:
preparing a chemical reaction apparatus including a horizontal flow reactor inside of which has been partitioned into multiple chambers continuously arranged in series by multiple partition plates, and a liquid content horizontally flows with an unfilled space being provided thereabove and continuous above the multiple partition plates in the reactor,
a microwave generator that generates microwaves, and
at least one waveguide that transmits the microwaves generated by the microwave generator to the unfilled space in the reactor,
wherein one or more weirs that are flow paths of the content are formed in an upper portion of each of the partition plates;
flowing the content over each of the multiple partition plates inside the reactor;
irradiating the content flowing inside the reactor with microwaves; and
changing an inclination angle of the reactor within a range in which, in each of the chambers, a weir height on an inlet side is higher than a weir height on an outlet side by at least an overflow depth at the partition plate on the outlet side, when the content flows inside the reactor.

2. The chemical reaction method according to claim 1, wherein, in the changing an inclination angle of the reactor, the inclination angle of the reactor is changed according to a state of the content.

3. The chemical reaction method according to claim 2, wherein the state is at least one of a temperature and a viscosity.

4. The chemical reaction method according to claim 1, wherein, in the changing an inclination angle of the reactor, the inclination angle of the reactor is changed according to a type of the content.

5. The chemical reaction method according to claim 1, wherein, in the changing an inclination angle of the reactor, the inclination angle of the reactor is changed according to an amount of the content that is loaded into the reactor per unit time.

\* \* \* \* \*